US011584772B2

(12) United States Patent
Meskys et al.

(10) Patent No.: US 11,584,772 B2
(45) Date of Patent: Feb. 21, 2023

(54) N⁴-MODIFIED CYTIDINE NUCLEOTIDES AND THEIR USE

(71) Applicant: VILNIUS UNIVERSITY, Vilnius (LT)

(72) Inventors: Rolandas Meskys, Vilnius (LT); Jevgenija Jakubovska, Uzukene (LT); Daiva Tauraite, Vilnius (LT)

(73) Assignee: VILNIUS UNIVERSITY, Vilnius (LT)

( * ) Notice: Subject to any disclaimer, the term of this patent is extended or adjusted under 35 U.S.C. 154(b) by 45 days.

(21) Appl. No.: 16/646,593

(22) PCT Filed: Sep. 12, 2018

(86) PCT No.: PCT/IB2018/056961
§ 371 (c)(1),
(2) Date: Mar. 12, 2020

(87) PCT Pub. No.: WO2019/053609
PCT Pub. Date: Mar. 21, 2019

(65) Prior Publication Data
US 2020/0270295 A1 Aug. 27, 2020

(30) Foreign Application Priority Data
Sep. 12, 2017 (LT) .................. LT2017 523

(51) Int. Cl.
C07H 19/10 (2006.01)
C12Q 1/68 (2018.01)
C07H 21/04 (2006.01)
C12N 15/10 (2006.01)

(52) U.S. Cl.
CPC ............ *C07H 19/10* (2013.01); *C07H 21/04* (2013.01); *C12N 15/1075* (2013.01); *C12Q 1/68* (2013.01)

(58) Field of Classification Search
CPC ........ C07H 19/10; C07H 21/00; C07H 21/04; C12N 15/1075; C12N 15/11; C12Q 1/68
See application file for complete search history.

(56) References Cited

U.S. PATENT DOCUMENTS

| | | | |
|---|---|---|---|
| 5,270,163 | A | 12/1993 | Gold et al. |
| 5,595,978 | A | 1/1997 | Draper et al. |
| 7,514,210 | B2 | 4/2009 | Holliger et al. |
| 2008/0167459 | A1 | 7/2008 | Fujihara et al. |
| 2013/0142796 | A1 | 6/2013 | Ray |
| 2014/0243389 | A1 | 8/2014 | Zakrzewski |
| 2016/0046973 | A1 | 2/2016 | Efcavitch et al. |
| 2016/0215013 | A1 | 7/2016 | Rohloff et al. |

FOREIGN PATENT DOCUMENTS

| | | |
|---|---|---|
| WO | 2011/028218 A1 | 3/2011 |
| WO | 2014/093924 A1 | 6/2014 |
| WO | 2015/051214 A1 | 4/2015 |
| WO | 2016/034807 A1 | 3/2016 |
| WO | 2016/164762 A1 | 10/2016 |

OTHER PUBLICATIONS

Stern et al. "The Role of the Minor Base N4-Acetylcytidine in the Function of the *Escheridia coli* Noninitiator Methionine Transfer RNA" The Journal of Biological Chemistry vol. 253, No. 17, Issue of Sep. 10, pp. 6132-6139. (Year: 1978).*
Ito et al. "Human NAT10 Is an ATP-dependent RNA Acetyltransferase Responsible for N4-Acetylcytidine Formation in 18S Ribosomal RNA (rRNA)" The Journal of Biological Chemistry vol. 289, No. 52, pp. 35724-35730, Dec. 26, 2014 (Year: 2014).*
International Search Report and Written Opinion, dated Dec. 10, 2018, from corresponding/related International Application No. PCT/IB2018/056961.
Chen, T. and Romesberg, F., "Directed polymerase evolution," FEBS Letters 588 (2014) 219-229.
Fonvielle, M. et al., "Decoding the Logic of the tRNA Regiospecificity of Nonribosomal FemXWv Aminoacyl Transferase," Angewamdte Chemie, Jul. 2010, 49, 5115-5119.
Supporting Information for: Fonvielle, M. et al., "Decoding the Logic of the tRNA Regiospecificity of Nonribosomal FemXWv Aminoacyl Transferase," Angewamdte Chemie, Jul. 2010, 49, 5115-5119.
Hansbury, E. et al., "Synthesis of Polydeoxy nucleotides using Chemically Modified Subunits," Biochimica et Biophysica Acta, 14999 (1970) 322-329.
Iannazzo, L. et al., "Synthesis of 3'-Fluoro-tRNA Analogues for Exploring Non-ribosomal Peptide Synthesis in Bacteria," Chembiochem. Feb. 9, 2015;16(3):477-86.
Marian, M., "Acetyl Derivatives of Nucleoside 5'-Triphosphates, I," Microchemical Journal 29, 219-227 (1984).
Nakatani, K. et al., Photochemistry of Benzophenone Immobilized in a Major Groove of DNA:Formation of Thermally Reversible Interstrand Cross-link, J. Am. Chem. Soc., vol. 124, No. 10, Sep. 2002.
Santarem, M. et al., "Synthesis of 3'-triazoyl-dinucleotides as precursors of stable Phe-tRNAPhe and Leu-tRNALeu analogues," Bioorganic & Medicinal Chemistry Letters 24 (2014) 3231-3233.
Schaller, H. and Khorana, H., "Studies on Polynucelotides. XXVII. The Stepwise Synthesis of Specific Deoxyribopolynucleotides (2). The Synthesis of Polynicelotides Containing Deoxycytidine and Deoxyguanosine in Specific Sequences and of Homologous Deoxycytidine Polynucelotides Terminating in Thymidine," Synthesis of Specific Deoxytibopolynucleotides, Dec. 5, 1963, pp. 3841-3851.

(Continued)

*Primary Examiner* — Jezia Riley
(74) *Attorney, Agent, or Firm* — Shannon K Stauffer

(57) ABSTRACT

Disclosed are N⁴-position modified cytidine nucleotides of formula (I). Provided herein are methods of chemical synthesis of N⁴-modified cytidine nucleoside triphosphates and their applications as well as uses of the cytidine analogues for the synthesis of modified nucleic acids. The nucleic acid molecule includes DNA, RNA or a combination of DNA/RNA. One of many applications of modified cytidine nucleotides described herein is enzyme selection, when an enzyme of interest bears an activity of an esterase, amidase, oxidoreductase, lyase, ligase or other enzymatic activity, formula (I) wherein the substituants are as defined in the appended claims.

19 Claims, 2 Drawing Sheets

Specification includes a Sequence Listing.

(56) References Cited

OTHER PUBLICATIONS

Zlatev, I. et al., "Efficient Solid-Phase Chemical Synthesis of 5'-Triphosphates of DNA, RNA, and their Analogues," Org. Lett., vol. 12, No. 10, 2010, pp. 2190-2193.

Supporting Information for: Zlatev, I. et al., "Efficient Solid-Phase Chemical Synthesis of 5'-Triphosphates of DNA, RNA, and their Analogues," Org. Lett., vol. 12, No. 10, 2010, pp. 2190-2193.

\* cited by examiner

SEQUENCE LISTING

```
<160> NUMBER OF SEQ ID NOS: 9

<210> SEQ ID NO 1
<211> LENGTH: 631
<212> TYPE: PRT
<213> ORGANISM: Unknown
<220> FEATURE:
<223> OTHER INFORMATION: Metagenomic origin

<400> SEQUENCE: 1

Met Ser Ser Leu Phe Ile Gly Gln Val Phe Ala Lys Thr Pro Glu Val
1               5                   10                  15

Gln Thr Ser Asp Leu Thr Gly Asn Thr Thr Cys Ser Asn Leu Val Gly
            20                  25                  30

Met Val Ile Pro Ala Asp Glu Ile Gly Leu Pro Thr Ser Gly Ala Thr
        35                  40                  45

Ile Thr Ser Ala Thr Leu Lys Ile Val Glu Asp Gly Ala Ile Lys Asp
    50                  55                  60

Ala Glu Tyr Cys Glu Val Leu Gly Ala Ile His Pro Val Asp Pro Thr
65                  70                  75                  80

Ala Pro Asp Ile Asn Phe Gln Val Asn Leu Pro Thr Asn Trp Asn Lys
                85                  90                  95

Lys Phe Leu Gln Phe Gly Gly Gly Tyr Phe Asn Gly Thr Val Arg Thr
            100                 105                 110

Gly Leu Gly Asn Pro Pro Ala Gly Asp Arg Lys Leu Gly Lys Asn Thr
        115                 120                 125

Pro Leu Ala Gln Gly Tyr Val Thr Phe Gly Ser Asp Ser Gly Asn Ser
    130                 135                 140

Thr Ala Pro Leu Asp Ala Ser Phe Gly Met Asn Asp Glu Ala Leu Lys
145                 150                 155                 160
```

```
Asn Phe Ala Gly Asp Gln Leu Lys Lys Thr Lys Asp Val Ala Leu Ala
                165                 170                 175

Leu Ala Asn Val Arg Tyr Asn Ala Val Pro Asp Gln Val Tyr Phe Ala
            180                 185                 190

Gly Gly Ser Glu Gly Arg Glu Gly Leu Phe Ile Val Gln Asn Phe
        195                 200                 205

Pro Asp Glu Tyr Asp Gly Val Ile Ser Val Tyr Pro Val Leu Asn Trp
    210                 215                 220

Ile Pro Lys Ala Leu Lys Asp Asn Arg Asp Ala Gln Ala Leu Tyr Lys
225                 230                 235                 240

Asn Asp Gly Glu Gly Trp Ile Ser Pro Glu Asn Asp Leu Ile Asn
            245                 250                 255

Glu Thr Val Phe Lys Ala Cys Asp Ser Leu Asp Gly Val Lys Asp Gly
            260                 265                 270

Ile Ile Ser Asn Thr Ser Glu Cys Ala Glu Lys Glu Asp Lys Ile Leu
        275                 280                 285

Asp Thr Leu Ser Glu Ser Leu Ser Glu Lys Gln Ile Glu Val Ile Lys
    290                 295                 300

Ser Phe Asn Gly Pro Met Glu Phe Asp Ile Gln Leu Ala Asn Asp Phe
305                 310                 315                 320

Thr Thr Met Pro Gly Tyr Ser Gln Leu Gln Gly Ala Asp Ile Gly Arg
                325                 330                 335

Leu Phe Gly Thr Arg Pro Ile Pro Gly Val Pro Val Val Ser Glu
            340                 345                 350

Ser Val Gly His Val Ile Asp Glu Gln Asp Ala Leu Met Gly Val Tyr
        355                 360                 365

Ser Asp Gln Val Ile Arg Tyr Lys Ile Thr Arg Asn Pro Asp Phe Asn
    370                 375                 380

Thr Leu Thr Phe Asp Pro Asn Glu Tyr Arg Glu Ile Leu Lys Ala
385                 390                 395                 400

Ser Asn Leu Leu Asp Val Thr Asp Pro Asn Ile Ser Glu Phe Arg Glu
            405                 410                 415

Asn Gly Gly Lys Leu Ile Leu Val His Gly Thr Glu Asp Glu Met Val
        420                 425                 430

Ala Pro Gln Gly Thr Ser Asp Tyr Tyr Ser Lys Leu Val Asn Glu Phe
    435                 440                 445

Gly Gln Glu Ser Leu Asp Glu Phe Ala Gln Tyr Tyr Leu Val Pro Gly
    450                 455                 460

Phe Ser His Gly Gly Asn Phe Thr Met Ser Ala Asn Leu Leu Gly
465                 470                 475                 480

Ala Leu Asp Ala Trp Val Val Asn Gly Asp Val Pro Ser Asn Leu Val
            485                 490                 495

Ala Glu Asp Gln Asn Ser Ala Thr Phe Gly Arg Thr Arg Pro Leu Cys
        500                 505                 510

Glu Tyr Pro Thr Tyr Pro Gln Tyr Asn Gly Ser Gly Asp Val Asn Ser
    515                 520                 525

Ala Ala Ser Phe Thr Cys Leu Lys Ala Asp Lys Asp Lys Asp Ile Ser
530                 535                 540

Ala Ser Asp Ile Gln Lys Leu Ile Glu Lys Phe Glu Val Asp Gly Glu
545                 550                 555                 560

Phe Ala Asn His Gly Thr Ala Arg Ser Leu Gln Ala His Leu Asp Ile
                565                 570                 575
```

Leu Ile Lys Leu Glu Ser Gln Glu Arg Glu Thr Val Asp Gln Ile Val
            580                 585                 590

Lys His Thr Gln Lys Phe Ile Lys Leu Leu Asp Asn His Lys Lys Asn
        595                 600                 605

Gly Lys Ile Thr Asp His Ala Tyr Asn Thr Leu Lys Glu Leu Ala Glu
        610                 615                 620

Ser Tyr Ile Lys Gln Ile Lys
625                 630

<210> SEQ ID NO 2
<211> LENGTH: 127
<212> TYPE: PRT
<213> ORGANISM: Unknown
<220> FEATURE:
<223> OTHER INFORMATION: Metagenomic origin

<400> SEQUENCE: 2

Met Glu Gln Leu Lys Phe Gln Lys Asn Trp Asn Asn Lys Cys Ser Cys
1               5                   10                  15

Asp Phe Phe Thr Thr Ile Arg Leu Lys Gly Pro Lys Tyr Thr Val Gly
                20                  25                  30

Lys Glu Leu Glu Met Arg Ile Tyr Lys Gly Gly Val Phe Gln Asn His
            35                  40                  45

Gly Met Ile Arg Val Ala Ser Leu Arg Pro Ile Gln Leu His Gln Ile
        50                  55                  60

Asn Glu Trp Ile Ser Arg Leu Asp Ser Gly Leu Ser Pro Glu Glu Leu
65                  70                  75                  80

Arg Ser Glu Leu Phe Tyr Met Tyr Lys Asp Lys Val Ala Asp Val Asn
                85                  90                  95

Lys Val Asp Phe Tyr Leu Ile Leu Cys Glu Arg Val Lys Ser Lys Pro
            100                 105                 110

Ile Gln Asn Ala Leu Phe Ser Thr Glu Ser Thr Pro Ala His Asp
        115                 120                 125

<210> SEQ ID NO 3
<211> LENGTH: 103
<212> TYPE: PRT
<213> ORGANISM: Escherichia coli

<400> SEQUENCE: 3

Met Gln Pro Asn Asp Ile Thr Phe Phe Gln Arg Phe Gln Asp Asp Ile
1               5                   10                  15

Leu Ala Gly Arg Lys Thr Ile Thr Ile Arg Asp Glu Ser Glu Ser His
                20                  25                  30

Phe Lys Thr Gly Asp Val Leu Arg Val Gly Arg Phe Glu Asp Asp Gly
            35                  40                  45

Tyr Phe Cys Thr Ile Glu Val Thr Ala Thr Ser Thr Val Thr Leu Asp
        50                  55                  60

Thr Leu Thr Glu Lys His Ala Glu Gln Glu Asn Met Thr Leu Thr Glu
65                  70                  75                  80

Leu Lys Lys Val Ile Ala Asp Ile Tyr Pro Gly Gln Thr Gln Phe Tyr
                85                  90                  95

Val Ile Glu Phe Lys Cys Leu
            100

<210> SEQ ID NO 4
<211> LENGTH: 35
<212> TYPE: DNA

```
<213> ORGANISM: Artificial Sequence
<220> FEATURE:
<223> OTHER INFORMATION: Template A

<400> SEQUENCE: 4
ccggaattaa aatctcccta tagtgagtcg tatta                         35

<210> SEQ ID NO 5
<211> LENGTH: 35
<212> TYPE: DNA
<213> ORGANISM: Artificial Sequence
<220> FEATURE:
<223> OTHER INFORMATION: Template G

<400> SEQUENCE: 5
ccggaattgg ggtctcccta tagtgagtcg tatta                         35

<210> SEQ ID NO 6
<211> LENGTH: 35
<212> TYPE: DNA
<213> ORGANISM: Artificial Sequence
<220> FEATURE:
<223> OTHER INFORMATION: Template C

<400> SEQUENCE: 6
ccggaattcc cctctcccta tagtgagtcg tatta                         35

<210> SEQ ID NO 7
<211> LENGTH: 35
<212> TYPE: DNA
<213> ORGANISM: Artificial Sequence
<220> FEATURE:
<223> OTHER INFORMATION: Template T

<400> SEQUENCE: 7
ccggaatttt tttctcccta tagtgagtcg tatta                         35

<210> SEQ ID NO 8
<211> LENGTH: 23
<212> TYPE: DNA
<213> ORGANISM: Artificial Sequence
<220> FEATURE:
<223> OTHER INFORMATION: T7 promoter primer

<400> SEQUENCE: 8
taatacgact cactataggg aga                                      23

<210> SEQ ID NO 9
<211> LENGTH: 20
<212> TYPE: DNA
<213> ORGANISM: Artificial Sequence
<220> FEATURE:
<223> OTHER INFORMATION: T7 terminator primer

<400> SEQUENCE: 9
ctagttattg ctcagcggtg                                          20
```

N⁴-MODIFIED CYTIDINE NUCLEOTIDES AND THEIR USE

FIELD OF THE INVENTION

The present invention relates generally to the field of nucleic acid chemistry, specifically to N⁴-position modified cytidine triphosphates. The present invention also relates to methods of making and using the same. The invention includes the use of the modified nucleotides for the synthesis of modified product, which can be an oligonucleotide, double- or single-stranded DNA or RNA fragment, or an aptamer. The present invention is based on the idea of using N⁴-modified cytidine triphosphates for the biosynthesis and application of modified nucleic acids. The present idea of biosynthesis and application of modified nucleic acids covers synthesis, modification and application of nucleic acid molecule comprising at least one cytosine nucleobase modification of the compounds described herein.

The invention is illustrated in several examples, using polymerases described herein. However, other polymerases, that are substrates for modified cytidine compounds, can be used.

BACKGROUND OF THE INVENTION

Oligonucleotides (ONs) are short DNA or RNA molecules which have found use in a wide variety of applications in the field of molecular biology, biotechnology, synthetic biology as well as medicine (diagnostics, antisense technology). ONs comprising natural nucleotides are usually unsuitable for application in the field of medicine due to their poor biostability and resistance to nucleases, e.g., blood serum nuclease. In order to improve ON's characteristics, e.g., stability, resistance, selectivity, catalytic activity, pharmacokinetic or pharmacodynamic characteristics, modified nucleotides are used. Moreover, limited chemical diversity of ONs plays an important role in various applications. As a result, ONs are modified to create a desirable diversity and to improve therapeutic ON's affinity, target specificity and distribution in the body, to control aggregation of ONs or to lower their toxicity.

Affinity and specificity are two major characteristics of any nucleic acid-based assay that determine its efficiency. Generally, sequence specificity and binding affinity anti-correlate with each other meaning that as affinity for the chosen target sequence increases, the likelihood of association with closely related but non-target sequences also increases (Lomakin and Frank-Kamenetskii, 1998). Such anti-correlation points out that the formation of nucleic acid duplexes and triplexes necessary for their functioning were either weak or nonspecific which in turn would contradict the methods and technologies which are based on nucleic acid interactions. This bizarre tendency can be explained using one of the two theories of biomolecular interactions. There are two modes of biomolecular interaction—shape complementarity or steric fit and nucleation-zipping. The shape complementarity concept means that biochemical recognition in enzyme-substrate, antigen-antibody and aptamer-small-molecule complexes is provided by a precise steric fit between surface regions of the binding ligand and the target (Koshland, 1995). The theory of steric fit is therefore considered to confirm the affinity-specificity correlation (von Hippel and Berg, 1986). The mechanism of nucleation zipping appears to be essential for the formation of nucleic acid duplexes and triplexes (Craig, Crothers, and Doty 1971; Alberti et al, 2002). By contrast to the steric fit, a strong zip with one irregular or missing link can still be fastened via bypassing this small mismatched part (Rougee et al, 1992). As a consequence, a problem of affinity-specificity is observed: both complexes correct and mismatched show comparable duplex formation efficiency.

Methods that are based on nucleic acid interactions can be divided into two major groups the one which ignores several mismatches and the other that requires high specificity. For example, genome analysis is a technology which is based on a very high affinity and specificity. Genome analysis is a very important methodology in biochemical and biomedical research area as well as provides knowledge about various pathogens and diseases. The basis of genome analysis is often detection of trace amounts of specific DNA sequences and therefore both affinity and specificity are essential. In order to discriminate between two almost identical DNA sequences (e.g. single nucleotide polymorphism), high sequence specificity factor is the main one. Therefore, it is essential to deal with affinity-specificity problem as a major constraining factor to further develop growing high-throughput technologies such as genome analysis.

Synthesis of modified nucleic acids is a way to reduce affinity-specificity anti-correlation. Compared to natural ONs, modified ONs have certain advantages in affinity and specificity, stability or other characteristics. For example, synthetic DNA-RNA-like polymer peptide nucleic acid (PNA) surpasses DNA properties. PNA does not possess a phosphodiester backbone as it is replaced with pseudopeptide polymer (N-(2-amino-ethyl)-glycine), which contains nucleobases connected to the backbone via methylencarbonyl bond. Compared to natural DNA, PNA shows enhanced affinity and specificity (Ratilainen et al, 2000) as well as it appears to be more stable on various surfaces (Kröger et al. 2002). PNA is uncharged and forms DNA-PNA duplexes without any need for additional ionic strength. As a consequence, contrary to natural ONs PNA easily hybridizes at a low salt concentration (Weiler et al. 1997). Hence favourable conditions for DNA-PNA duplex formation might be optimised by destabilizing DNA-DNA complexes. By doing so, PNA based detection probes would become superior compared to DNA probes (Pokorski et al. 2004).

Similarly to PNA, locked nucleic acid (LNA) also exhibits high affinity and specificity (Braasch and Corey 2001; Petersen and Wengel 2003; Rakesh N. Veedu and Wengel 2010; Veedu and Wengel 2009). The ribose moiety of an LNA nucleotide contains an additional covalent bridge connecting 2' oxygen and 4' carbon, thus conformational motion is repressed. As a result LNA possesses higher affinity and specificity for complementary DNA or RNA and forms duplexes more easily. In addition, carbocyclic LNA analogues such as ethylene-bridged nucleic acids (ENAs) are particularly advantageous in terms of resistance to blood serum nucleases, e.g. ENAs can circulate in blood more than 48 h compared to natural ONs (<3 h) or LNAs (>9 h).

In addition to PNA and LNA, other synthetic DNA/RNA-like oligomers show enhanced properties such as resistance to nucleases, stability, synthesis cost or diversity over natural counterparts. These artificial oligomers are morpholino nucleic acids (Summerton 1989), hexitol and 1,5-anhydrohexitol nucleic acids (Lescrinier et al. 2000), tricyclo-DNA (Renneberg and Leumann 2002), unlocked nucleic acids (UNAs) (Langkjaer, Pasternak, and Wengel 2009), arabinose nucleic acids (ANAs), treose nucleic acids (TNAs), etc. (Wilson and Keefe, 2006).

ONs are becoming increasingly important and promising molecular tool with widespread applications as nucleic acid therapeutics in the field of antisense therapy, RNA interference (RNAi), ribozyme or aptamer technology (Sharma, Rungta, and Prasad 2014; Rayburn and Zhang 2008). Antisense therapy and RNAi are very efficient processes regulating gene expression. Broadly speaking, the mechanism of action is based on interaction between synthetic ON and a complementary target messenger RNA (mRNA) so that gene silencing occurs. In order to use synthetic ON as a therapeutic agent it should meet several requirements. First of all, ON should cross cell membrane and specifically interact with its target only. Moreover, ON cannot be toxic to the host cell as well as stay stable both in the intercellular and extracellular environment. It should be noted that the cost of ON synthesis plays an important role. Consequently, ON should be described by superior features such as high affinity and specificity to the target, resistance to intra- and extracellular nucleases (endo- and exo-nucleases also). ONs cannot interact with other accessory biomolecules and should exhibit properties needed for trans-membrane transfer. As a result, to improve all this stringent properties and functions of a therapeutic ON a lot attention is being paid to the development of synthetic ONs.

Up to date, antisense ONs can be classified into 3 generations—first, second and third (Sharma, Sharma, and Singh, 2014; Chery, 2016). The first generation antisense ONs were developed to increase resistance to nucleases. The standard chemical modification to synthesize first generation antisense ON is replacement of the oxygen atom of the sugar-phosphate backbone with either a sulphur group (phosphorothioate ON (PS-ON)) (Xie et al. 2012; Rahman et al. 2012; E. De Clercq, Eckstein, and Merigan 1969) or methyl group (methyl phosphonates) (Monn and Schurch 2007; Shoji et al. 1991). These ONs have more resistance to nucleases; carry negative charges that ease their cell delivery and peripheral distribution (Yu et al. 2007). Compared to natural ONs, first generation ONs have advantages, however they still possess poor affinity and specificity.

To eliminate shortcomings of the first generation ONs, second generation ONs were developed. Along with PS backbone, additional modifications of nucleobases and monosaccharides are present in the second generation ONs which help to increase affinity and specificity. The most commonly used second generation modifications are 2'-O-methyl (2'-OME) and 2'-O-methoxyethyl (2'-OMOE) modified ribose (Frank Bennett 2007). Other modifications include changes in C5-position of pyrimidines (Moulds et al. 1995; Flanagan, Kothavale, and Wagner 1996) and C7-position of purines (Buhr et al. 1996). Second generation antisense ONs are reported to have a higher affinity and specificity, better tissue uptake and lower toxicity.

Third generation ONs, for example PNAs, LNAs and phosphoroamidate-morpholino oligomers (PMO) are characterised by modifications of the furanose ring. The modifications were made to improve the nuclease resistance, biostability, target affinity and specificity, and other pharmacokinetic profiles of the third generation ONs.

Similarly to antisense therapy, the most commonly used modifications in RNAi are third generation backbone modifications such as boranophosphates and phosphorotioates as well as substitution of 2'-OH group of monosaccharide with OME-, OMOE-, F-, etc. (Bumcrot et al. 2006).

In addition to the widespread application of modified ONs, modified nucleosides or nucleotides are equally important molecular tools in modern medicine. Modified nucleosides/nucleotides come as one of the forms of reverse transcriptase inhibitors which in turn are a class of antiretroviral drugs. Unlike the natural nucleotides these analogues lack a 3'-OH group and thus act as chain terminators. Hence, viral DNA synthesis is halted. Modified nucleoside/nucleotide analogues are used for the treatment of AIDS and during highly active antiretroviral therapy (HAART). For example, acyclovir is a modified guanine based gold standard antiretroviral drug for the treatment of herpes virus infections (Elion et al. 1977; Schaeffer et al. 1978). 3'-substituted-2', 3'-dideoxynucleosides are used for the treatment of HIV infections (Herdewijn et al. 1987; Balzarini et al. 1988), while L-nucleosides are known as specific hepatitis B virus inhibitors (Bryant et al. 2001). Plenty of other nucleoside and nucleotide analogues are used in the antiretroviral therapy (Erik De Clercq and Field 2006; Hurwitz and Schinazi 2013).

Currently there are three FDA approved ON-based drugs used in medicine. Pegaptanib (Macugen®) is an ON that specifically interacts with vascular endothelial growth factor (VEGF) and is used for the treatment of age-related macular degeneration. It is the first FDA approved polyethylenglycol (PEG)-conjugated aptamer, bearing 2'-F and 2'-O-methyl modifications of pyrimidine nucleotide (Pat. No. US20130142796; Tucker et al. 1999). Fomivirsen (Vitravene™) is a PS-ON which binds to the complementary sequence of the cytomegalovirus (CMV) mRNA. It blocks translation of viral mRNA and thus is used for the treatment of CMV retinitis (U.S. Pat. No. 5,595,978; Marwick 1998). Mipomersen (Kynamro™) is also a PS-ON though with different modifications—2'-OMOE and 5-methylcytosine (Pat. No. US2014243389). Mipomirsen targets mRNA of an apolipoprotein B (apo-B) and therefore apo-B synthesis is inhibited. This artificial ON is used to treat hypercholesterolemia (McGowan et al. 2012). There are many other synthetic ONs which are undergoing clinical trials (Chery 2016).

Ribozymes are RNA molecules that are capable of catalysing biochemical reactions. These catalytic RNA molecules mimic function of enzymes at the nucleic acid level. Since ribozymes are often used in medicine, various modifications are tested to improve ribozyme biostability and resistance to nucleases. In the case of ribozymes, selection of modifications is limited by the fact that catalytic activity can be disrupted. Modification of ribozyme can lead to either damaged or improved catalytic activity (Beigelman et al. 1995).

Aptamers are DNA or RNA ONs that form stable and unique tertiary structure and specifically bind to its target molecules, e.g., proteins, drugs, living cells, small organic or inorganic molecules (Patel and Suri 2000; Sun and Zu 2015). Systematic evolution of ligands by exponential enrichment (SELEX) is an in vitro selection technique for evolving aptamers (U.S. Pat. No. 5,270,163; Tuerk and Gold 1990; Ellington and Szostak 1990). A great interest in SELEX technology induced substantial progress towards more efficient, cheaper and easier-to-handle selection methods (Darmostuk et al. 2015). To obtain an aptamer of various desirable properties, e.g. high affinity to its target or selectivity, random ON library is subjected to repeated rounds of ONs selection and identification. Properties of selected aptamer, for example stability, overall charge of nucleic acid molecule, hydrophobicity or hydrophilicity, lipophilicity, thermostability or resistance to nucleases, can be further improved by post-SELEX technology that utilizes additional chemical modification of the selected ON (Gao et al. 2016; Kusser 2000). Unfortunately post-modification increases the risk to impair the tertiary structure of an aptamer thus changing essential ON characteristics (e.g. affinity, selectivity or catalytic activity) (Avino et al. 2012). To overcome this complication and to expand structural and functional diversity of ONs an alternative strategy referred to as mod-SELEX is performed using a library of ONs with the chemical substitutions already present (Keefe and Cload 2008). Various chemical modifications enrich starting ON pool, however, renders amplification step of SELEX challenging, as modified nucleotides are usually poor substrates for DNA and RNA polymerases (Lapa, Chudinov, and Timofeev 2016). A wide variety of upgraded approaches of conventional SELEX have been developed such as capillary electrophoresis, magnetic bead-based, cell, in vivo, one-round, post-, photo-, in silico, blended, mirror-image or Spiegelmer, chimeric, indirect, crossover, click SELEX, etc. There is no unique SELEX method to fulfil all requirements as each SELEX owns its benefits and drawbacks.

Aptamers have been used in numerous investigations, from acting as therapeutics in medicine to various applications in biotechnology, e.g. chromatography, mass spectrometry, capillary electrophoresis, as acoustic, optical or signalling aptamers, etc. (Tombelli, Minunni, and Mascini 2005). However it is believed that the major field of aptamer's application is clinical therapy. Besides clinical therapy, aptamers are used in many other applications; such as detection of viral or bacterial infections (Kiilerich-Pedersen et al. 2013; Rotherham et al. 2012), detection of cancer biomarkers (Chang, Donovan, and Tan 2013), detection of proteins in Western blot (Shin et al. 2010), as capture agents in microarrays and biosensors (Jung et al. 2013; Sosic et al. 2013; Q. Wang et al. 2014), chromatography and surface plasmon resonance (Zhao et al. 2008; H. Chen et al. 2014) or as in vivo imaging agents (Hong et al. 2011).

Three types of nucleotide modifications are used to generate modified aptamers; the backbone, sugar or nucleobase modifications (Wilson and Keefe 2006). Similarly to therapeutic ONs, modification of sugar-phosphate backbone leads to an increased resistance to nucleases. However, the main task is to create three-dimensional architecture alternatives and expand variety. For example, aptamers with an F, $NH_2$ or O-MOE residue at the 2' position of ribose are used (Wilson and Keefe 2006). To obtain high affinity and specificity aptamers with unique tertiary structure modification of nucleobases is performed. The most common modifications are C5-substituted pyrimidines (e.g. 5-pentynyl-, 5-N-carbamoyl-, 5-borate-, 5-iodo-, 5-tyrosyl-, 5-imidazole-, 5-carboxamide-, 5-naphtylaminocarbonyl-, 5-benzylaminocarbonyl-) and purines bearing various residues at the C7 and C8 positions (Pat. No. US20160215013; Lapa, Chudinov, and Timofeev 2016). There are several reasons to select and modify C5 position of pyrimidines and C7 position of purines. It has been shown that both of these positions orient the modified residue towards the major groove of the double helix; this arrangement is commonly considered to minimize interference with aptamer activity. Moreover, dNTPs with C5/C7 substituents have demonstrated the best compatibility with most RNA and DNA polymerases. As a consequence such modified analogues can be amplified and used in SELEX.

Substitution of C5-position of pyrimidine nucleotide is one of the most commonly used base modifications in aptamer technology. SOMAmers (Slow Off-rate Modified Aptamers) are aptamers that distinguish themselves having very low dissociation rate constants and containing various functional groups at the 5-position of the uracil (J. C. Rohloff et al. 2014; Kuwahara et al. 2006). Functional moieties conjugated at the uracil ring mimic amino acid side chains and thus create unique intramolecular motifs and make direct contacts with proteins. This creates a somamer/aptamer which specifically interacts with extremely hydrophobic or charged molecule, e.g. protein. To increase C5-modified nucleotide repertoire copper(I)-catalysed azide-alkyne cycloaddition or Click chemistry may be applied (Tolle et al. 2015). Click chemistry is based on utilization of 5-ethynyl-dUTP that being a component of an ON may be further modified. This prevents incompatibility of modified substituent and polymerase.

There are several aspects regulating the selection of nucleobase position to be modified. The most important rule is to preserve the Watson-Crick base geometry and complementarity with natural bases. Contrary to modified nucleotides, unnatural nucleotides are not limited to natural pair formation and may generate completely new unnatural base pairs. Thus unnatural base pairs can expand the genetic alphabet by creating a third base pair (next to A:T and C:G) (Yamashige et al. 2012; Seo et al. 2011; Malyshev et al. 2012). Using six instead of four natural nucleotides, unnatural nucleotides could increase the functionality of aptamers by providing additional chemical and structural diversity. It has been demonstrated that during ExSELEX (genetic alphabet Expansion for SELEX) incorporation of unnatural base pairs into starting pool can yield aptamers with greatly augmented affinities to its targets (Kimoto et al. 2013; Georgiadis et al. 2015).

It should be specified that the compatibility of the modified nucleotides and ONs with DNA or RNA polymerases used in the SELEX process is a primary concern (Obeid et al. 2010; Bergen et al. 2012; Lam, Hipolito, and Perrin 2008). It is important that not only modified dNTPs should act as good substrates for polymerases but modified templates must also be further amplified. Since polymerases play a significant role in molecular biology it is obvious that a gold standard for polymerase (thermostability, efficiency, fast synthesis, accuracy, processing power, use of modified substrates) is being searched for. Before starting SELEX process with modified NTPs or dNTPs, commercially available polymerases are tested first. It is known that C5/C7-position of nucleotides are the most permissive sites for modification that are accepted by several known polymerases such as Vent, KOD Dash, KOD XL, Taq DNA and T7 RNA polymerases (Lipi et al. 2016). However, usually these polymerases are efficient only under specific optimal conditions. Investigation of structural and functional properties of polymerases leads to understanding of the nature of interactions between polymerase and its substrate as well as it helps to learn the mechanism of polymerization. Such knowledge in turn becomes a basis for generation of mutant polymerases following rational design principles (Kries, Blomberg, and Hilvert 2013; Khoury et al. 2014). Although rational design is based on the ability to predict crucial amino acids, it does not guarantee polymerase improvement (Samish et al. 2011). An alternative strategy to upgrade proteins known as directed evolution mimics the process of Darwin's natural selection (Jackel, Kast, and Hilvert 2008). Directed evolution is based on repeated cycles of generation of huge molecular diversity and selection of proteins based on the desired properties. Directed evolution is analogous to natural selection since the link between genotype and phenotype is preserved (Leemhuis, Kelly, and Dijkhuizen 2009). So during in vitro evolution specific selection pressure is created, e.g., utilization of modified nucleotides instead of natural ones. In the directed molecular evolution of polymerases, selection by compartmentalized self-replication (CSR) has commonly been used (Pat. No. US7514210132; Ghadessy, Ong, and Holliger 2001). By applying selection pressure, for instance replacing natural nucleotides with various analogues, mutant polymerases that are able to incorporate modified NTPs can be selected and become right for SELEX (T. Chen and Romesberg 2014; Laos, Thomson, and Benner 2014). CSR is based on simple feedback—only genes encoding active polymerases are replicated, whereas inactive variants fail to amplify their own genes and disappear from the gene pool. Using CSR a variety of polymerases have been evolved that differ in substrate specificity: DNA polymerase specific for modified dNTP (Obeid et al. 2010; Bergen et al. 2012; Meek, Rangel, and Heemstra 2016), RNA polymerases capable of incorporation of modified NTP (Chelliserrykattil and Ellington 2004), DNA polymerase acting as RNA polymerase (Xia et al. 2002), polymerase demonstrating DNA and RNA polymerase and reverse transcriptase activities (Ong et al. 2006).

Although CSR is a very powerful method for evolution of polymerases, it lacks versatility for evolution in vitro of other proteins. However insertion of an extra stage into the CSR cycle before the polymerase reaction allows its application to enzymes other than polymerases. Usually, in cooperative/coupled compartmentalized self-replication or otherwise known as compartmentalized partnered-replication (CPR), synthetic circuits are linked to the production of Taq DNA polymerase so that evolved circuits that most efficiently drive Taq DNA polymerase production are enriched by exponential amplification during a subsequent emulsion PCR step (Ellefson et al. 2014). Despite the fact that this approach is especially sensitive, examples of CPR are rare in literature, since it is complicated to design such a cooperative system that links activity of a random enzyme to its amplification by polymerase. DNA binding proteins regulate the majority of cellular processes (e.g. replication, transcription, epigenetic modification, DNA damage repair) therefore investigation of DNA-protein interactions is important for biotechnological progress as well as fundamentally. To investigate interactions between DNA and proteins a cross-linking strategy has been applied that is based on conversion of weak noncovalent interactions to covalent bonds by formation of covalent heteroconjugate. To characterize such conjugates properly DNA-protein complex must be stable, chemical bonds must connect nucleobases and amino acid side chains positioned at small distance only, and covalent complex must preserve native steric shape (Steen and Jensen 2002). Structural analysis of nucleic acid-protein heteroconjugates enables the understanding of cross-linking stoichiometry, finding out the domains of nucleic acid binding proteins and specific amino acid residues that interact with nucleic acid molecule.

Photochemical cross-linking (or photocrosslinking) is one of the most commonly used methods to analyse DNA-protein complexes and mechanisms of interaction. Since native proteins and nucleic acids absorb UV light at 250-280 nm, they can be connected photochemically but still maintain their tertiary structure. However, there are some drawbacks such as low yield and photochemical or oxidative degradation of covalent complex. To bypass such difficulties, photoactive chemical group that absorbs >300 nm UV light is used. This photoactive chemical group is introduced into nucleic acid or protein molecule by several approaches. One strategy allows incorporation of additional heterobifunctional photoactive cross-linking agents, e.g. 2-iminothiolane (Wower et al. 1981) or 4-mercaptobutyrimidate (Traut et al. 1973), for joining the DNA-protein complex. In order to apply this strategy, cross-linking agent is delivered after formation of ON-protein complex so that free amino acid side chain groups may interact. When complex is excited at 350-365 nm UV light, formation of covalent bonds occurs. An alternative approach to connect DNA to a protein is to utilize photosensitive DNA or protein analogues. Since both in vivo and in vitro synthesis of ONs is an advanced technology, photoactive group is introduced into nucleic acids more often. There is a vast amount of different photosensitive nucleotide analogues and photosensitive modifications. The most common nucleotide analogues are azido-, thio-, bromo- and iodo-substituted nucleobases bearing nucleotides (Meisenheimer and Koch 1997). Another way to photosensitize nucleotide is by incorporating photosensitive chemical group such as psoralen (S. S. Sastry et al. 1993), diazirine (Shigdel, Zhang, and He 2008) or benzophenone (S. Sastry it Ross 1998).

Benzophenone is probably the most widely used and versatile photophore in organic chemistry, bioorganic chemistry, and material science due to its unique photochemical properties (Sergentu et al. 2014). The efficiency of photosensitization depends on two operations: ability of the agent to acquire and maintain excited triplet state and subsequent energy transfer which is strongly connected to interactions between photosensitive molecule and the surrounding chemical groups. It has been demonstrated that benzophenone absorbs at 365 nm UV light leading to triplet state transition that is characterized by long half-life. As a consequence benzophenone has a wide range of applications as a photoinitiator (Gyorgy Dorman et al. 2016; Khanum, Shashikanth, and Deepak 2004; Ranganatha et al. 2013). Due to its properties benzophenone is used in bioconjugation and immobilization, proteome and interactome profiling, surface and polymer chemistry, DNA photolabelling, etc. (Gyorgy Dorman et al. 2016). Application of benzophenone expanded to in vivo protein labelling by genetically encoding benzophenone-containing amino acid (Chin et al. 2002; Lang and Chin 2014; L. Wang et al. 2001). Moreover, since benzophenone initiates transformations of surface C—H bonds, it is a very important photophore used to develop surface technologies, and applied in biotechnology, optics, electronics and photonics (Turgeon, Harley, and Bailey 2014; G. Dorman and Prestwich 2000).

Benzophenone is activated in a UV range (350-365 nm) that does not damage cells, proteins or nucleic acids. Benzophenone photochemically reacts with sterically accessible C—H bonds found in the sugar-phosphate backbone of DNA or in the side chains of amino acids. As a result, benzophenone has been utilized along with various biomolecules for photoimmobilization of ONs and peptides for creating cell trapping systems (Herman et al. 2011), functionalizing surfaces for the detection of antigens and pathogenic bacteria (Konry et al. 2005) or generating antimicrobial coating for textiles (Dhende et al. 2011). DNA microarrays are a growing field of biotechnology and therefore different immobilization methods are being developed. Photochemical immobilization of ONs onto benzophenone-derivatives coated surface seems to be very promising in this field (Renberg et al. 2009; Marcon et al. 2010). Unfortunately, little is known about ONs bearing benzophenone modification, immobilization or cross-linking with various biomolecules (Nakatani, Dohno, and Saito 1999; Nakatani, Yoshida, and Saito 2002). Such ONs could be synthesized either by chemical pattern or during enzymatic catalysis. As a result benzophenone-modified specific ONs could be immobilized onto different supports and used for detection of complementary sequences in various samples.

Growing technologies of ONs stimulate generation of alternative nucleotide modifications. Although modifications of 05/07/08 nucleotide positions are analysed sufficiently, little is known about substitutions of other nucleotide positions. Furthermore, there still is a need to evolve new polymerases that not only incorporate modified nucleotides during PCR but also are efficient, accurate and productive and would improve mod-SELEX. CSR is a widespread approach to evolve mutant polymerases which incorporate modified nucleotides, yet there is a lack of alternatives to evolution in vitro of other proteins. Moreover, to investigate protein-protein, protein-nucleic acid interactions or to apply immobilization technologies conjugation/cross-linking technologies need to be further improved. The present invention provides knowledge about new nucleotide modifications by introducing N$^4$-modified cytidine analogues and its applications.

SUMMARY OF THE INVENTION

The present invention describes N$^4$-position modified cytidine triphosphates and the methods of making and using the same.

In one aspect, the invention describes N$^4$-position modified cytidine nucleotides having common structural Formula I:

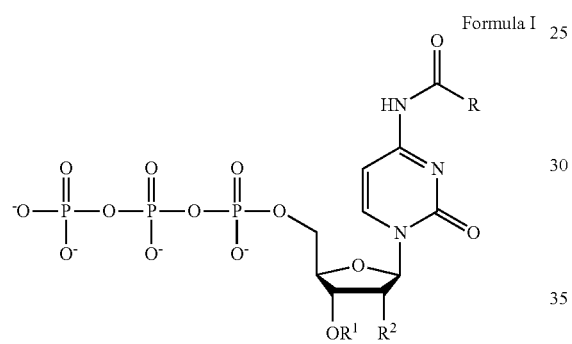

Formula I wherein
R is independently selected from the group consisting of:
—(CH$_2$)$_n$—CH$_3$, wherein n is 0, 1, 2, 3, 4, 5, 6, 7, 8, 9 or 10;

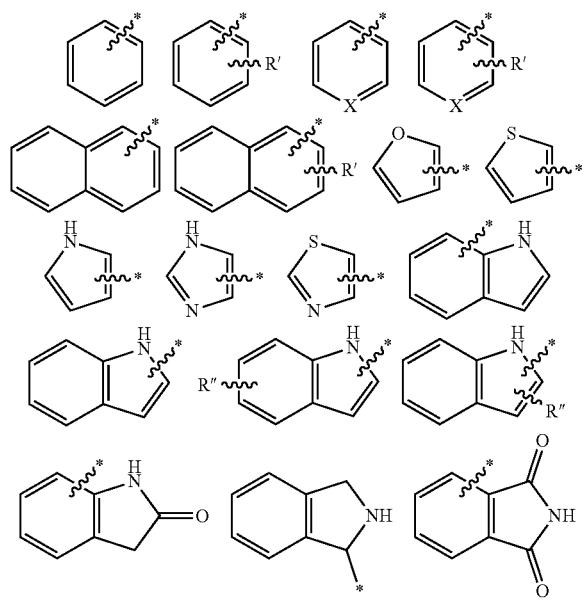

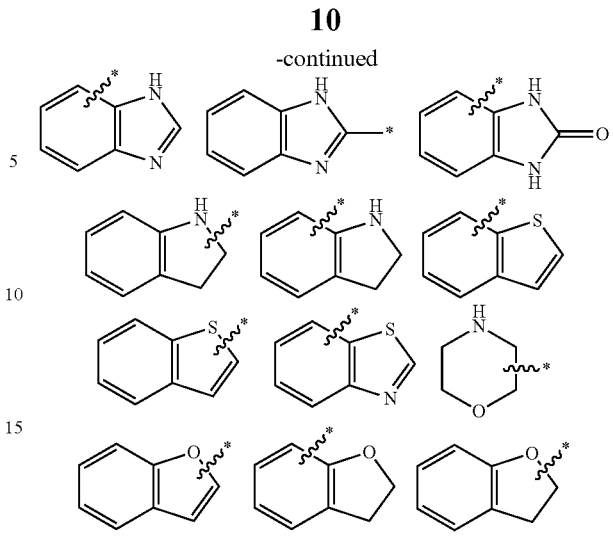

wherein * is the point of attachment of the R group;
wherein R' is independently selected from the group consisting of:

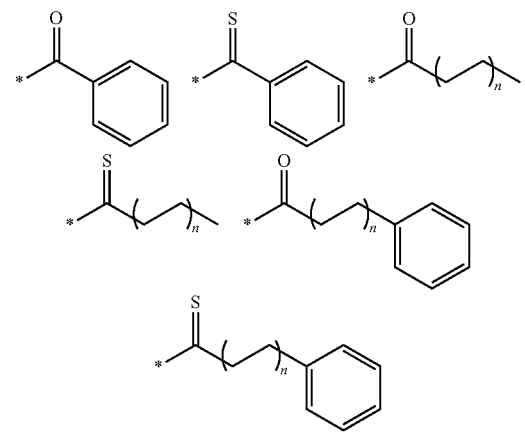

wherein n is 0, 1, 2, 3, 4, 5, 6, 7, 8, 9 or 10; and wherein * is the point of attachment of the R' group to the R group; and wherein R" is independently selected from the group consisting of —H, —CH$_3$, —NH$_2$, —OH, —Cl and —Br;

X is independently selected from the group consisting of —CH= and —NH=;

R$^1$ is independently selected from the group consisting of —H, —OAc, —OBz, —Me and —Et;

R$^2$ is independently selected from the group consisting of —H, —OH, —OMe and —OEt.

In another aspect, this invention describes nucleic acid molecule having any one of the compounds described above. In a related aspect, the nucleic acid molecule can be single stranded or double stranded. In another aspect, the nucleic acid molecule comprises DNA, RNA or a combination thereof.

In a related aspect, a nucleic acid molecule is from 10 to 4000 nucleotides in length.

In another aspect, a nucleic acid molecule is an aptamer.

In another aspect, the invention describes nucleic acid molecule having the structural Formula IA:

Formula IA

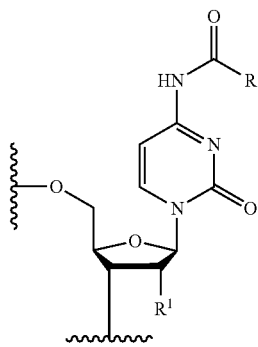

wherein
R is independently selected from the group consisting of:
—(CH$_2$)$_n$—CH$_3$, wherein n is 0, 1, 2, 3, 4, 5, 6, 7, 8, 9 or 10;

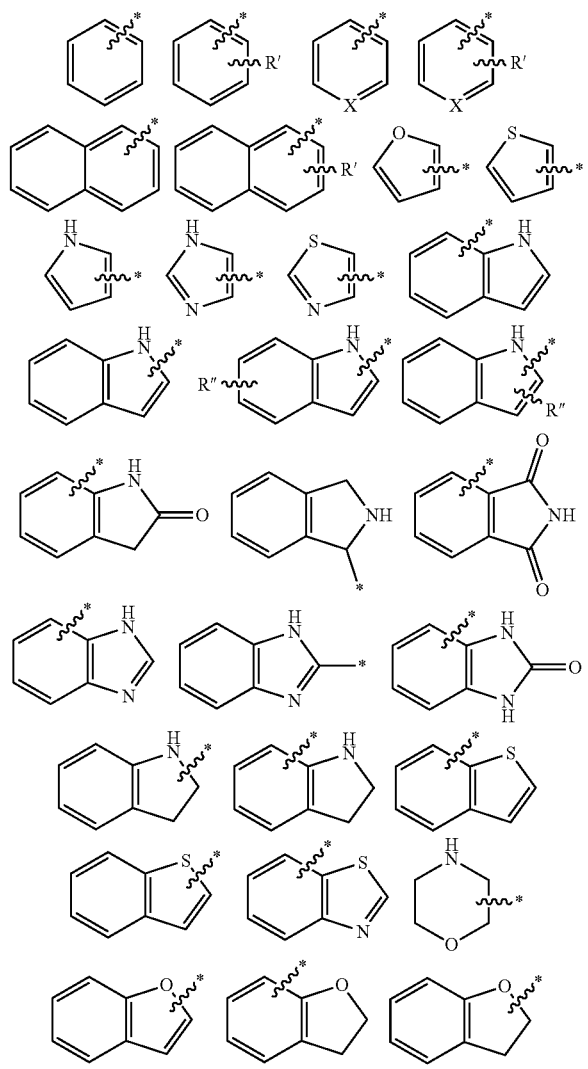

wherein * is the point of attachment of the R group;
wherein R' is independently selected from the group consisting of:

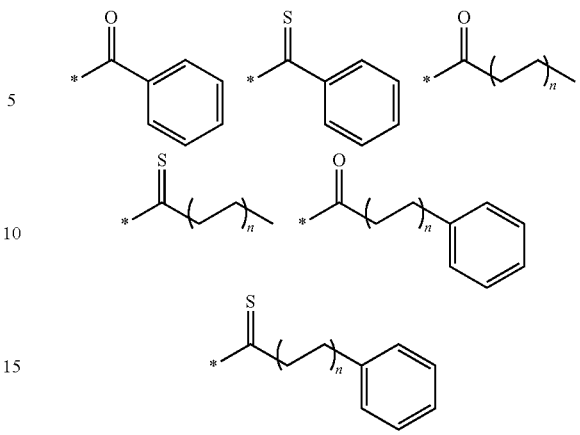

wherein n is 0, 1, 2, 3, 4, 5, 6, 7, 8, 9 or 10; and wherein * is the point of attachment of the R' group to the R group; and wherein
R" is independently selected from the group consisting of —H, —CH$_3$, —NH$_2$, —OH, —Cl and —Br;
X is independently selected from the group consisting of —CH= and —NH=;
R$^1$ is independently selected from the group consisting of —H, —OH, —OMe and —OEt.

In another aspect, the invention describes a method of using N$^4$-modified cytidine nucleotides for the synthesis of modified oligonucleotides. In a related aspect, the nucleic acid molecule can be single stranded or double stranded. In another aspect, the nucleic acid molecule comprises DNA, RNA or a combination thereof.

In yet another aspect, the invention describes a method of synthesizing modified oligonucleotides by primer extension.

The present invention further provides for a method of usage of N$^4$-modified cytidine nucleotides for enzyme selection. Enzymes can either i) remove modification; ii) or use modification for the synthesis of modified oligonucleotide. In another aspect, the invention describes an enzyme having a specification for the enzymatic activity of esterase, amidase, oxidoreductase, lyase or other enzymatic activity showing ability to convert modified cytidine nucleotide to cytidine nucleotide. In yet another aspect, the invention describes an enzyme capable of decomposing modified nucleotide to the natural one and either i) modified residue or ii) decomposed modified residue, or in other words an enzyme can further degrade modified residue yielding several constituents.

In another aspect, the invention describes a selection method of enzymes, namely polymerases, when an enzyme under selection carries out polymerization of nucleic acids using N$^4$-modified cytidine analogues. Activity of such enzyme is unique by the fact that N$^4$-modified cytidine nucleotide is used instead of natural cytidine nucleotide, and the reaction product is a nucleic acid molecule comprising any one of the compounds described above. In yet another aspect, the invention describes a compartmentalized self-replication as a selection method covering selection of the gene encoding polymerase and a subsequent amplification of that gene, or a compartmentalized partnered-replication as a selection method covering selection of the gene encoding an enzyme that removes or otherwise alters the modification, and an additional polymerase performing compartmentalized amplification of the gene encoding enzymes under selection. In a related aspect, enzyme selection by compartmentalized (self)replication takes place in an emulsion, and amplification of the gene encoding an enzyme is performed during emulsion PCR.

The present invention further describes the method of targeted labelling of a modified biomolecule, including labelling of the reporter group that leads to the identification of a labelled biomolecule among unlabelled.

In another aspect, the invention describes a site-directed mutagenesis. The invention further provides for a method of attachment of modified nucleotide to an oligonucleotide or longer DNA fragment, and subsequent amplification of modified nucleic acid molecule when a modified nucleobase is coupled to the other modified nucleobase regardless of complementarity principle (A couples with T and C couples with G), for example, instead of interaction with guanine modified cytidine nucleobase interacts with other nucleobase of nucleic acid molecule.

The present invention further describes a method of application of $N^4$-modified cytidine nucleotides as a cross-linking agent. In a related aspect, the invention provides for an incorporation of $N^4$-modified cytidine nucleotide analogues into the structure of an oligonucleotide and subsequent cross-linking to various surfaces. As used herein, the term "surface" refers to a biomolecule such as protein or nucleic acid surface as well as appropriately pre-treated or natural surfaces (e.g. polyethylene, polystyrene, etc.).

In yet another aspect, the invention describes a method of using $N^4$-modified cytidine nucleotides for the detection of DNA fragmentation. Fragmented cellular DNA molecules composed of modified nucleotides described above could be further labelled using additional dye molecule. This detection method would allow labelling of cells that have been already initiated signalling cascades leading to apoptosis.

BRIEF DESCRIPTION OF THE FIGURES

In order to illustrate the major features of the invention two accompanying figures are presented.

DETAILED DESCRIPTION OF THE INVENTION

LIST OF ABBREVIATIONS USED HEREIN

Figure 1:
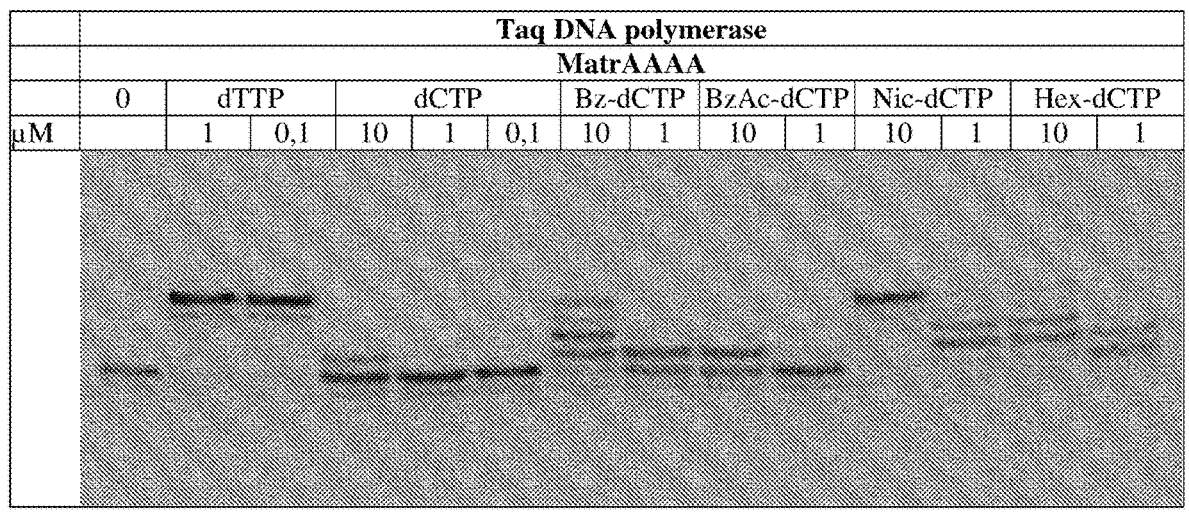
FIG. 1. A polyacrylamide gel image of a primer extension assay using template-dependent Taq DNA polymerase as described in the Materials and Methods section Example 8.
Figure 2:
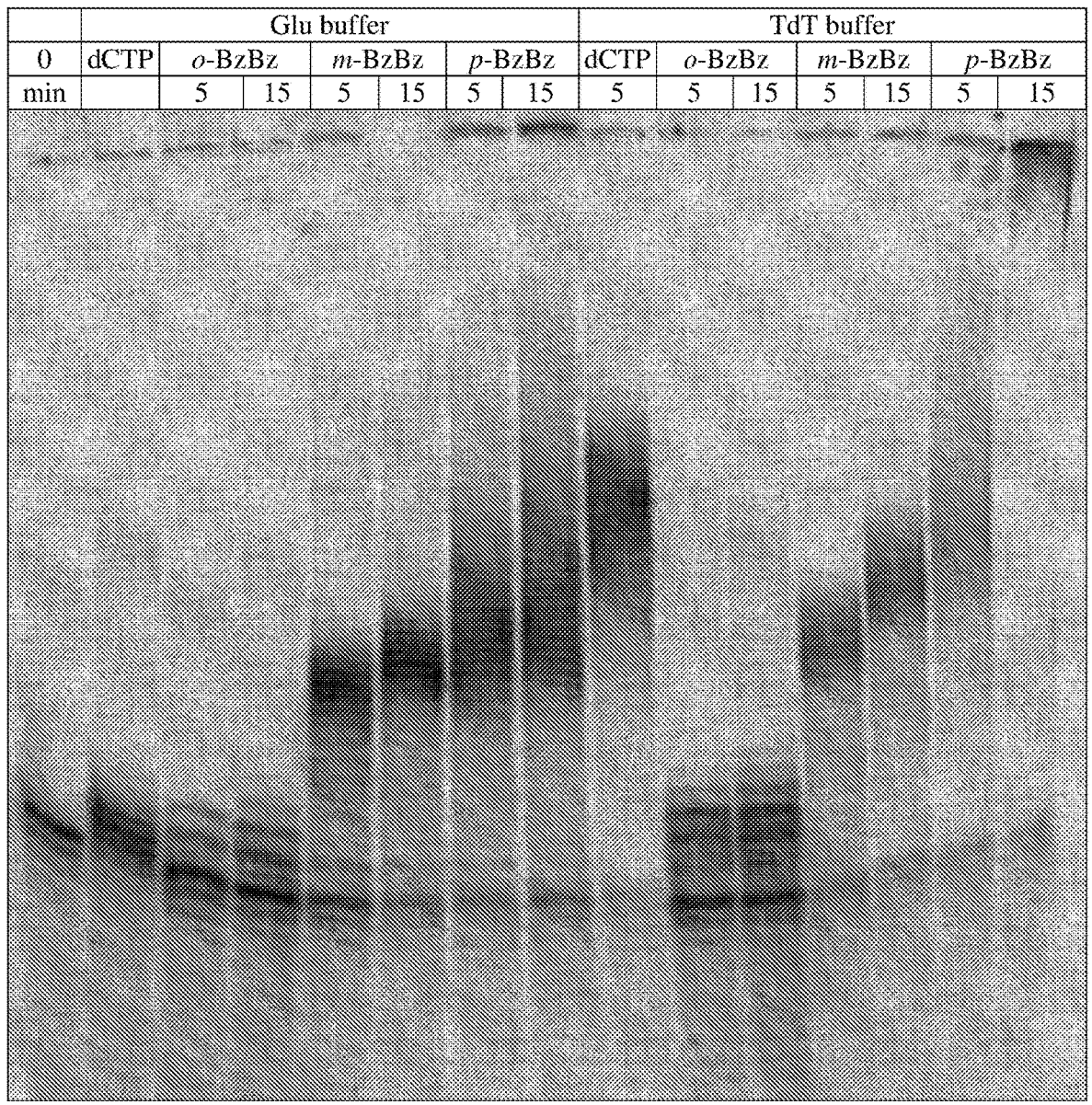
FIG. 2. A polyacrylamide gel image of a primer extension assay using template-independent terminal deoxynucleotidyl transferase as described in the Materials and Methods section Example 9.

2'-OME 2'-O-methyl-
2'-OMOE 2'-O-metoxyethyl-
Apo-B—apolipoprotein B
BSA—bovine serum albumin
CFU—colony-forming unit
DCC—N,N'-dicyclohexylcarbodiimide
DEAE—diethylaminoethyl
DMF—N,N-dimethylformamide
DTT—dithiothreitol
EDTA—ethylendiaminetetraacetic acid
EtOAc—ethylacetate
IPTG—isopropyl-β-D-1-thiogalactopyranoside
$L_0$ initial library
LNA—locked nucleic acid
mRNR—messenger RNR
NMR—nuclear magnetic resonance
ON—oligonucleotide
PAGE—polyacrylamide gel electrophoresis
PEG—polyethylene glycol
PMO—phosphoroamidate-morpholino oligomer
PNA—peptide nucleic acid
$POCl_3$—phosphorus oxychloride
PS—phosphorothioate
RNRi—RNR interference
SDS—sodium dodecylsulfate
SELEX—systematic evolution of ligands by exponential enrichment)
TBA—tributylamine
TBAPF—tributylamonium pyrophosphate
TBE Tris-borate-EDTA buffer solution
TdT—terminal deoxynucleotidyl transferase
TLC—thin-layer chromatography Scheme I for the chemical synthesis of compounds provided in the present invention is described herein:

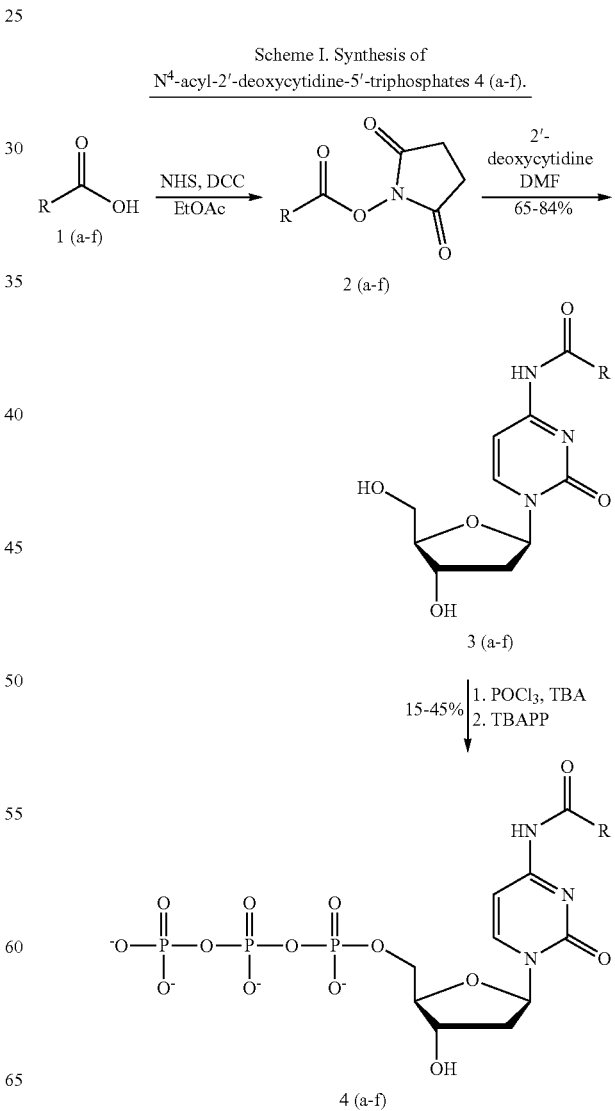

Scheme I. Synthesis of $N^4$-acyl-2'-deoxycytidine-5'-triphosphates 4 (a-f).

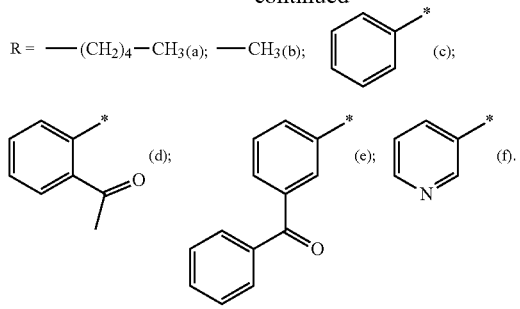

R = —(CH$_2$)$_4$—CH$_3$(a); —CH$_3$(b); (c); (d); (e); (f).

Modified at 4-position of heterocyclic base 2'-deoxycytidines were prepared by acylation of 2'-deoxycytidine with appropriate activated ester of carboxylic acid. After purification of synthesized nucleosides by column chromatography, N$^4$-acyl-2'-deoxycytidines were isolated in 65-84% yields. The synthesized nucleosides were phosphorylated with phosphorus oxychloride and the obtained monophosphates were treated with tributylammonium pyrophosphate. The synthesized modified nucleosides triphosphates were purified by ion exchange chromatography on DEAE Sephadex A-25 columns with a linear gradient of LiCl as a mobile phase. The yields of synthesized N$^4$-acyl-2'-deoxycytidine-5'-triphosphates were 15-45%. The structures of new compounds were proved by NMR spectroscopy and HPLC-MS analysis.

As used herein, the term "nucleotide" refers to a ribonucleoside or deoxyribonucleoside triphosphate, or its modified variations or analogues thereof. Nucleotides comprise one of purine (e.g. adenine, guanine, hypoxanthine or any variations thereof) or pyrimidine (cytosine, thymine, uracil or any variations thereof) nucleobases.

As used herein, the term "nucleic acid" refers to DNA, RNA, DNA-RNA hybrid, modified DNA or modified RNA molecule. The term "oligonucleotide" includes oligoribonucleotide or oligodeoxyribonucleotide.

As used herein, the terms "modified", "modification", "modify", and any variations thereof, when used in reference to an oligonucleotide means that the nucleotide contains additional chemical group that is not present in the natural nucleosides (i.e., adenosine, guanosine, cytidine, thymidine, uridine), and at least one of the four constituent nucleotide bases (i.e., adenosine, guanosine, cytidine, thymidine, uridine) of the oligonucleotide is an analogue. Additional modifications can include sugar-phosphate backbone modifications, methylations, unusual base-pairing combinations, 3' and 5' modifications (e.g., capping), etc. Further, any of the hydroxyl groups ordinary present on the sugar (e.g., ribose, deoxyribose or other) of a nucleotide may be replaced by a phosphonate group or a phosphate group; protected by standard protecting groups; or activated by additional bonds. The 3' and 5' terminal OH groups can be phosphorylated or substituted with amines or other organic functional groups. Oligonucleotides can also contain analogous forms of ribose or deoxyribose sugars, including 2'-O-methyl-, 2'-O-allyl-, 2'-O-ethyl-, 2'-O-propyl-, 2'-metoxyethyl-, 2'-O-fluoro-, 2'-O-amino-, 2'-O-azido- pentoses, α-anomeric sugars, other aldopentoses (i.e., arabinoses, xyloses, lyxoses), pyranoses, acyclic analogues.

Modification can be performed on a nucleotide or an ON. ON can be additionally modified, for example, conjugating with other molecules.

As used herein, the term "aptamer" refers to a non-naturally occurring nucleic acid that has a desirable action on a target molecule. A desirable action includes, but is not limited to, i) binding of the target, ii) catalytically changing the target, iii) reacting with the target in a way that modifies or alters the target or the functional activity of the target, iv) covalently attaching to the target (as in a suicide inhibitor), and v) facilitating the reaction between the target and another molecule.

As used herein, the term "compartmentalized self-replication" refers to a selection method of evolution in vitro, that includes self-replication of active polymerase encoding genes only under selection pressure, and the amplification occurs in different compartments. The term "compartment" refers to a miniature drop of water that is present in an emulsion, i.e., mixture of water and oil solutions. Emulsion can be prepared from various water-based and oil-based solutions. It is considered that such emulsion contains $10^{10}$/mL water drops/compartments on average. Further, it is assumed that statistically one water droplet contains a single cell. Except for the cell, water drop is also provided with reagents for emulsion PCR such as buffer solution, nucleotides, gene encoding polymerase, primers and other supplementary enzymes or reagents. Supplementary enzymes or reagents may refer to various components necessary for PCR or optional selection reactions. Additional selection steps and necessary components are mentioned in Examples section but are not limited to Examples and may contain other variations.

The term "selective pressure" refers to an individual experimental condition such as, but not limited to, higher or lower temperature, different reaction components, number and duration of wash steps that is used during selection procedure and that leads to amplification of those variants which stay active under selective pressure. As used herein, the terms "selective pressure" and "evolutionary pressure" are used interchangeably.

As used herein, the term "compartmentalized partnered-replication" refers to a selection or screening method of evolution in vitro, when only active protein variants out of entire protein library generate specific conditions for additional polymerase to amplify genes encoding active protein variants, and when amplification occurs in compartments.

The term "enzyme library" refers to a collection of plasmids that are composed of a vector and gene of interest. An enzyme library can be a metagenomic library or mutant library. Metagenomic library is used for screening of novel enzymes that are found in microorganisms originated from different environmental places such as soil, seawater, sludge, etc. Mutant library is used for the selection of variants of a known protein/enzyme that contains novel mutations which improve desirable properties or functions.

As used herein, the term "cross-linking" refers to a formation of a covalent bond between two polymers. The term "polymer" refers to any kind of biological molecule (protein, nucleic acid, lipid, etc.) or non-biological polymer, for example, polyester, polystyrene, polyethylene, poly(methylmethacrylate), and others.

EXAMPLES

The following examples are provided to illustrate certain particular features and/or embodiments. These examples should not be construed to limit the invention to the particular features or embodiments described.

Example 1

Preparation of N⁴-hexanoyl-2'-deoxycytidine-5'-triphosphate (Compound 4a)

This example provides the methods for making the modified triphosphate according to the Scheme II.

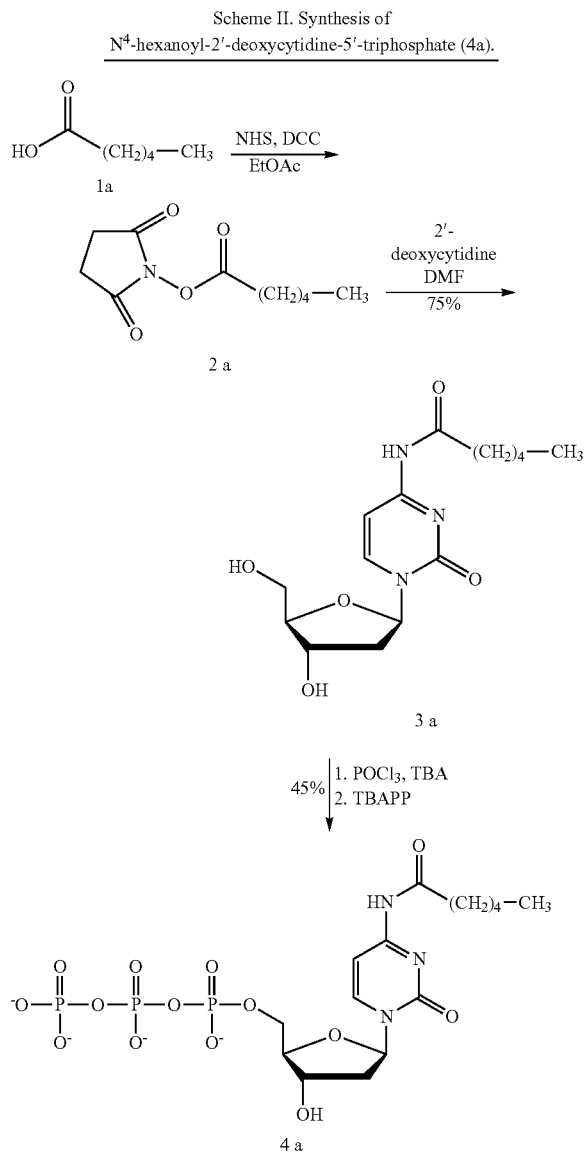

Synthesis of N⁴-hexanoyl-2'-deoxycytidine 3a. Hexanoic acid (58 mg, 0.5 mmol), N-hydroxysuccinimide (NHS, 63 mg, 0.55 mmol) and N,N'-dicyclohexylcarbodiimide (DCC, 113 mg, 0.55 mmol) were dissolved in 15 mL of ethyl acetate (EtOAc) and stirred at room temperature for 20 h. The formed precipitate was filtered and activated acid 2a remained in the filtrate. The ethyl acetate was evaporated under reduced pressure. The activated hexanoic acid was dissolved in 1.5 mL of N,N-dimethylformamide (DMF), and 103 mg (0.45 mmol) of 2'-deoxycytidine was added. The mixture was stirred at 30-35° C. temperature for 24-48 h. Completion of the reaction was determined by thin-layer chromatography (TLC, chloroform/methanol, 9/1). After the reaction was completed (TLC), DMF was evaporated under reduced pressure. The residue was dissolved in chloroform and purified by column chromatography (silica gel, chloroform/methanol mixture, 10:0→10:1). Yield 122 mg (75%). MS (ESI+): m/z 326.10 [M+H]+; 324.10 [M−H]−. UV $\lambda_{max}$ 247; 298 nm. ¹H-NMR (DMSO-d₆): δ=0.86 (t, 3H, J=6.8 Hz, CH₃); 1.22 (m, 4H, CH₂); 1.52 (m, 2H, CH₂); 2.02 (m, 1H, CH₂); 2.29 (m, 1H, CH₂); 2.39 (t, 2H, J=7.3 Hz, CH₂); 3.61 (m, 1H, CH₂); 3.74 (m, 1H, CH₂); 3.93 (m, 2H, CH); 5.04 (s, 1H, OH); 5.26 (s, 1H, OH); 6.11 (t, 1H, J=6.0 Hz, CH); 7.23 (d, 1H, J=7.5 Hz, CH=CH); 8.32 (d, 1H, J=7.5 Hz, CH=CH); 10.83 (s, 1H, NH). ¹³C-NMR (DMSO-d₆): δ=14.26; 22.29; 24.61; 25.69; 31.18; 36.24; 61.42; 70.40; 86.60; 88.37; 95.72; 145.41; 154.93; 162.77; 174.39.

Synthesis of N⁴-hexanoyl-2'-deoxycytidine-5'-triphosphate 4a.

Synthesized N⁴-hexanoyl-2'-deoxycytidine (98 mg, 0.3 mmol) 3a, tributylamine (TBA, 143 μL, 0.6 mmol) were suspended in 1.5 mL of trimethylphosphate and cooled to 0-4° C. temperature. Phophorous oxychloride (POCl₃, 56 μL, 0.6 mmol) was added to the cooled mixture and stirred at 0-4° C. temperature for 60-120 min. Completion of the reaction was determined by TLC, 1,4-dioxane/2-propanol/water/NH₄OH, 4/2/2/1. After the formation of N⁴-hexanoyl-2'-deoxycytidine monophosphate, 72 μL (0.3 mmol) of TBA and 3 mL of 0.5 M tributylammonium pyrophosphate solution (TBAPP, 1.5 mmol) in acetonitrile were added dropwise. After stirring for 10-15 min the reaction mixture was poured into ice-water and neutralized with saturated sodium bicarbonate solution to pH 6-7. The reaction mixture was purified by ion exchange chromatography on DEAE-Sephadex A25 column (30 mL) with a linear gradient (0.05-0.4 M) of LiCl as the mobile phase. The product was eluted with 0.25-0.3 M LiCl, the purity of fractions were monitored by TLC (1,4-dioxane/2-propanol/water/NH₄OH, 4/2/5/1). The pure fractions were combined. The solution was concentrated under reduced pressure to several millilitres and poured into a 30-40 mL mixture of acetone/methanol, 4/1. The formed precipitate was collected by centrifugation (4000 rpm, 10 min) and twice washed with a mixture of acetone/methanol, 4/1. The nucleotide was dissolved in 2-3 mL of water, evaporated under reduced pressure and neutralized with 1 M sodium hydroxide solution to pH 7.0. The synthesized nucleotide after purification by ion exchange chromatography was purified once again by reverse phase chromatography (C-18 cartridges, water/methanol mixture, 10:0→10:2). The triphosphate was eluted with 15-20% methanol/water mixture, and the purity of fractions were monitored by TLC (1,4-dioxane/2-propanol/water/NH₄OH, 4/2/5/1). The fractions with pure N⁴-hexanoyl-2'-deoxycytidine triphosphate were combined, and the solvents were removed under reduced pressure. The triphosphate was dissolved in 2-3 mL of water, neutralized with 1 M sodium hydroxide solution to pH 7.0 and filtered (0.45 μm PTFE). The absorption of purified nucleotide was measured, the concentration and amount of synthesized compound was calculated. Yield 5.2 mL, 26 mM, 135 mmol (45%). MS (ESI+): m/z 566.05 [M+H]+; 564.05 [M−H]−. UV $\lambda_{max}$ 246; 298 nm. ¹H-NMR (D₂O): δ=0.75 (t, 3H, J=7.0 Hz, CH₃); 1.20 (m, 4H, CH₂); 1.54 (m, 2H, CH₂); 2.24 (m, 1H, CH₂); 2.38 (t, 2H, J=7.4 Hz, CH₂); 2.40 (m, 1H, CH₂); 4.09 (m, 1H, CH); 4.14 (m, 2H, CH₂); 4.54 (m, 1H, CH); 6.15 (t, 1H, J=6.2 Hz, CH); 7.26 (d, 1H, J=7.5 Hz, CH=CH); 8.28 (d, 1H, J=7.5 Hz, CH=CH). ³¹P-NMR (D₂O): δ=−20.54 (t, J=19.7 Hz, Pβ); −9.23 (d, J=18.7 Hz, Pα), −7.19 (d, J=19.8 Hz, Pγ).

Example 2

Synthesis of N⁴-acetyl-2'-deoxycytidine-5'-triphosphate (Compound 4b)

The compound was prepared as described in example 1 (compound 4a) from acetic acid 1b. N⁴-Acetyl-2'-deoxycytidine, 3b. Yield 105 mg, (78%). MS (ESI⁺): m/z 270.10 [M+H]⁺; 268.10 [M−H]⁻. UV $\lambda_{max}$ 246; 298 nm. ¹H-NMR (DMSO-d₆): δ=2.04 (m, 3H, CH₃); 2.11 (m, 1H, CH₂); 2.41 (m, 1H, CH₂); 4.12 (m, 3H, CH, CH₂); 4.46 (m, 1H, CH); 5.04 (s, 1H, OH); 5.27 (s, 1H, OH); 6.12 (t, 1H, J=6.0 Hz, CH); 7.20 (d, 1H, J=7.5 Hz, CH=CH); 8.26 (d, 1H, J=7.5 Hz, CH=CH); 10.81 (s, 1H, NH). ¹³C-NMR (DMSO-d₆): δ=23.98; 39.72; 63.59; 69.73; 85.35; 87.10; 98.35; 145.57; 156.96; 162.57; 173.34.

N⁴-Acetyl-2'-deoxycytidine-5'-triphosphate, 4b. Yield 3.2 mL, 23 mM, 74 mmol (25%). MS (ESI⁺): m/z 510.00 [M+H]⁺; 508.00 [M−H]⁻. UV $\lambda_{max}$ 243; 296 nm. ¹H-NMR (D₂O): δ=2.08 (m, 3H, CH₃); 2.21 (m, 1H, CH₂); 2.40 (m, 1H, CH₂); 4.11 (m, 3H, CH, CH₂); 4.47 (m, 1H, CH); 6.11 (t, 1H, J=6.0 Hz, CH); 7.20 (d, 1H, J=7.5 Hz, CH=CH); 8.26 (d, 1H, J=7.5 Hz, CH=CH. ³¹P-NMR (D₂O): δ=−20.61 (t, J=18.8 Hz, Pβ); −10.94 (d, J=18.7 Hz, Pα); −5.24 (d, J=18.9 Hz, Pγ).

Example 3

Synthesis of N⁴-benzoyl-2'-deoxycytidine-5'-triphosphate (Compound 4c)

The compound was prepared as described in example 1 (compound 4a) from benzoic acid 1c.

N⁴-Benzoyl-2'-deoxycytidine, 3c. Yield 132 mg, (80%). MS (ESI+): m/z 332.10 [M+H]⁺; 330.10 [M−H]⁻. UV $\lambda_{max}$ 256; 303 nm. ¹H-NMR (DMSO-d₆): δ=2.34 (m, 2H, CH₂); 3.74 (m, 2H, CH₂); 4.05 (m, 1H, CH); 4.54 (m, 1H, CH); 5.03 (s, 1H, OH); 5.26 (s, 1H, OH); 6.12 (t, 1H, J=6.1 Hz, CH); 7.26 (d, 1H, J=7.5 Hz, CH=CH); 7.40 (t, 2H, J=7.6 Hz, CH); 7.65 (t, 1H, J=7.5 Hz, CH); 7.87 (dd, 2H, J=8.4; 1.2 Hz, CH); 8.29 (d, 1H, J=7.5 Hz, CH=CH); 10.64 (s, 1H, NH). ¹³C-NMR (DMSO-d₆): δ=38.77; 61.78; 70.31; 85.90; 86.86; 96.25; 128.13; 128.60; 131.75; 135.04; 143.10; 155.02; 168.20; 169.17.

N⁴-Benzoyl-2'-deoxycytidine-5'-triphosphate, 4c. Yield 6.5 mL, 17 mM, 110 mmol (37%). MS (ESI⁺): m/z 572.05 [M+H]⁺; 570.00 [M−H]⁻. UV $\lambda_{max}$ 257; 303 nm. ¹H-NMR (D₂O): δ=2.28 (m, 1H, CH₂); 2.50 (m, 1H, CH₂); 4.18 (m, 3H, CH, CH₂); 4.54 (m, 1H, CH); 6.19 (t, 1H, J=6.3 Hz, CH); 7.39 (d, 1H, J=7.5 Hz, CH=CH); 7.48 (t, 2H, J=7.8 Hz, CH); 7.61 (t, 1H, J=7.5 Hz, CH); 7.82 (dd, 2H, J=8.4; 1.2 Hz, CH); 8.34 (d, 1H, J=7.5 Hz, CH=CH). ³¹P-NMR (D₂O): δ=−20.69 (t, J=19.1 Hz, Pβ); −10.95 (d, J=18.7 Hz, Pα); −5.33 (d, J=19.1 Hz, Pγ).

Example 4

Synthesis of N⁴-benzoyl-2-acetyl-2'-deoxycytidine-5'-triphosphate (Compound 4d)

The compound was prepared as described in example 1 (compound 4a) from 2-acetylbenzoic acid 1d.

N⁴-Benzoyl-2-acetyl-2'-deoxycytidine, 3d. Yield 121 mg, (65%). MS (ESI⁺): m/z 374.05 [M+H]⁺; 372.10 [M−H]⁻. UV $\lambda_{max}$ 265; 307 nm. ¹H-NMR (DMSO-d₆): δ=2.09 (s, 3H, CH₃); 2.35 (m, 2H, CH₂); 3.63 (m, 2H, CH₂); 3.90 (m, 1H, CH); 4.25 (m, 1H, CH); 5.09 (s, 1H, OH); 5.30 (s, 1H, OH); 6.16 (t, 1H, J=6.2 Hz, CH); 6.85 (d, 1H, J=7.5 Hz, CH=CH); 7.53 (m, 2H, CH); 7.62 (m, 1H, CH); 7.80 (m, 1H, CH); 8.44 (d, 1H, J=7.5 Hz, CH=CH); 10.57 (s, 1H, NH). 13C-NMR (DMSO-d₆): δ=28.25; 39.10; 61.67; 70.32; 86.07; 86.86; 96.25; 127.18; 131.68; 131.98; 135.50; 142.76; 154.60; 168.40; 171.88; 177,60.

N⁴-Benzoyl-2-acetyl-2'-deoxycytidine-5'-triphosphate, 4d. Yield 2.8 mL, 17 mM, 48 mmol (16%). MS (ESI⁺): m/z 614.00 [M+H]⁺; 612.00 [M−H]⁺. UV $\lambda_{max}$ 267; 307 nm. ¹H-NMR (D₂O): δ=1.97 (s, 3H, CH₃); 2.29 (m, 1H, CH₂); 2.49 (m, 1H, CH₂); 4.14 (m, 3H, CH, CH₂); 4.32 (m, 1H, CH); 6.19 (t, 1H, J=6.0 Hz, CH); 7.39 (d, 1H, J=7.6 Hz, CH=CH); 7.57 (m, 1H, CH); 7.66 (m, 2H, CH); 7.78 (m, 1H, CH); 8.33 (d, 1H, J=7.6 Hz, CH=CH). ³¹P-NMR (D₂O): δ=−20.26 (t, J=18.5 Hz, Pβ); −10.80 (d, J=18.5 Hz, Pα); −4.91 (d, J=18.2 Hz, Pγ).

Example 5

Synthesis of N⁴-benzoyl-3-benzoyl-2'-deoxycytidine-5'-triphosphate (Compound 4e)

The compound was prepared as described in example 1 (compound 4a) from 3-benzoylbenzoic acid 1e.

N⁴-Benzoyl-3-benzoyl-2'-deoxycytidine, 3e. Yield 152 mg, (70%). MS (ESI⁺): m/z 436.10 [M+H]⁺; 434.10 [M−H]⁻. UV $\lambda_{max}$ 255; 303 nm. ¹H-NMR (DMSO-d₆): δ=2.07 (m, 1H, CH₂); 2.33 (m, 1H, CH₂); 3.63 (m, 2H, CH₂); 3.89 (m, 1H, CH); 4.25 (m, 1H, CH); 5.06 (s, 1H, OH); 5.29 (s, 1H, OH); 6.15 (t, 1H, J=6.3 Hz, CH); 7.38 (d, 1H, J=7.0 Hz, CH=CH); 7.60 (m, 2H, CH); 7.73 (m, 1H, CH); 7.77 (m, 2H, CH); 7.83 (d, 2H, J=8.2 Hz, CH); 8.16 (d, 2H, J=8.2 Hz, CH); 8.44 (d, 1H, J=7.0 Hz, CH=CH); 11.45 (5, 1H, NH). ¹³C-NMR (DMSO-d₆): δ=41.10; 61.42; 70.39; 86.78; 88.45; 107.18; 129.12; 129.22; 129.84; 130.19; 133.62; 136.96; 140.46; 145.21; 163.02; 168.56; 188.32; 195.80.

N⁴-Benzoyl-3-benzoyl-2'-deoxycytidine-5'-triphosphate, 4e. Yield 6 mL, 20 mM, 120 mmol (40%). MS (ESI⁺): m/z 676.05 [M+H]⁺; 674.05 [M−H]⁻. UV $\lambda_{max}$ 257; 302 nm. ¹H-NMR (D₂O): δ=2.25 (m, 1H, CH₂); 2.45 (m, 1H, CH₂); 4.17 (m, 3H, CH, CH₂); 4.53 (m, 1H, CH); 6.15 (t, 1H, J=6.0 Hz, CH); 7.,31 (d, 1H, J=7.0 Hz, CH=CH); 7.47 (m, 2H, CH); 7.63 (m, 4H, CH); 7.90 (m, 1H, CH); 8.06 (m, 2H, CH); 8.31 (d, 1H, J=7.0 Hz, CH=CH). ³¹P-NMR (D₂O): δ=−20.58 (t, J=18.5 Hz, Pβ); −10.91 (d, J=18.4 Hz, Pα); −5.28 (d, J=18.4 Hz, Pγ).

Example 6

Synthesis of N⁴-nicotinoyl-2'-deoxycytidine-5'-triphosphate (Compound 4f)

The compound was prepared as described in example 1 (compound 4a) from nicotinic acid 1f.

N⁴-Nicotinoyl-2'-deoxycytidine, 3f. Yield 140 mg, (84%). MS (ESI⁺): m/z 333.05 [M+H]⁺; 331.05 [M−H]⁻. UV $\lambda_{max}$ 253; 307 nm. ¹H-NMR (DMSO-d₆): δ=2.07 (m, 1H, CH₂); 2.33 (m, 1H, CH₂); 3.62 (m, 2H, CH₂); 3.89 (m, 1H, CH); 4.25 (m, 1H, CH); 5.09 (t, 1H, J=5.1 Hz, OH); 5.30 (d, 1H, J=4.2 Hz, OH); 6.14 (t, 1H, J=6.3 Hz, CH); 7.33 (s, 1H, CH=CH); 7.55 (dd, 1H, J=7.9; 4.9 Hz, CH); 8.33 (d, 1H, J=8.0 Hz, CH); 8.42 (d, 1H, J=7.3 Hz, CH=CH); 8.77 (d, 1 H, J=4.9 Hz, CH); 9.11 (s, 1H, CH); 11.50 (s, 1H, NH). ¹³C-NMR (DMSO-d₆): δ=41.39; 49.06; 61.41; 70.38; 86.73; 88.45; 96.53; 128.89; 129.68; 136.61; 145.58; 149.84; 158.38; 163.17; 173.48.

N⁴-Nicotinoyl-2'-deoxycytidine-5'-triphosphate, 4f. Yield 3 mL, 15 mM, 45 mmol (15%). MS (ESI⁺): m/z 573.00 [M+H]⁺; 571.00 [M−H]⁻. UV $\lambda_{max}$ 256; 305 nm. ¹H-NMR (D₂O): δ=2.26 (m, 1H, CH₂); 2.47 (m, 1H, CH₂); 4.42 (m, 4H, CH₂, CH); 6.16 (t, 1H, J=6.1 Hz, CH); 7.37 (d, 1H, J=7.5 Hz, CH=CH); 7.51 (dd, 1H, J=7.8; 5.1 Hz, CH); 8.22 (d, 1H, J=8.1 Hz, CH); 8.35 (d, 1H, J=7.5 Hz, CH=CH); 8.64 (s, 1H, CH); 8.89 (s, 1H, CH). $^{31}$P-NMR (D$_2$O): δ=−20.67 (t, J=18.5 Hz, Pβ); −10.92 (d, J=18.5 Hz, Pα); −6.06 (d, J=18.2 Hz, Pγ).

Example 7

Selection of Enzymes Hydrolysing Amide Bond of Modified dNTP

The present invention describes a method of enzyme selection in vitro. In vitro enzyme selection takes place in an emulsion during compartmentalized replication. Enzymes undergoing selection catalyse the hydrolysis of an amide bond present in a modified dNTP (4a-e) yielding natural dNTP. After hydrolysis step, all four natural dNTPs necessary for PCR are formed in water droplets (or compartments) of an emulsion. An additional DNA polymerase amplifies gene encoding enzyme that is undergoing selection.

Metagenomic library (L$_0$) used for the selection contained a set of plasmids that have been constructed using pET28b expression vector and DNA fragments which were obtained by hydrolysing chromosomal DNA with restriction endonucleases. L$_0$ library was transformed into E. coli BL21 (DE3) bacteria, bacterial cell number was estimated and was equated to the size of L$_0$. L$_0$ was evaluated to contain ~5×10$^7$ variants.

Metagenomic library was then prepared for the enzyme selection procedure. 5×10$^9$ metagenomic library cells were grown in 50 mL LB medium with appropriate antibiotic. E. coli BL21 (DE3) bacteria were incubated at 37° C. on a rotator until OD$_{600}$ reached 0.7. Then gene expression was induced by adding IPTG to a final concentration of 0.5 mM. Bacteria were grown for 2 hours at 37° C., then the culture was chilled on ice. Spectrophotometric quantification of bacterial density (colony forming units (CFU/mL)) was performed. The cell culture was aliquoted into 1 mL and cells were harvested by centrifugation at 3300 g for 1 min at 4° C. Cells were suspended in 1 mL of 0.9% NaCl solution, centrifuged and once again re-suspended in 0.5 mL of 1× PCR buffer solution. Freshly prepared lysozyme solution (20 μg/μL) was added to the cell suspension and incubated for 10 min at 37° C. Lysozyme-processed cell suspension was then used for emulsion PCR.

Oil-surfactant mixture (50 mL) was prepared by thoroughly mixing mineral oil (97.95%), ABIL EM 90 (2%) and Triton X-100 (0.05%).

PCR mixture was prepared by mixing the following components to the final concentration: 1× HF PCR buffer solution, 0.33 μM T7prom primer, 0.33 μM T7ter primer, 2 mM natural dNTP's each (dATP, dTTP, dGTP), 3 mM modified dCTP, 0.5 μg/mL BSA, 0.6 units of Phusion DNA polymerase (Thermo Fisher Scientific). Primer sequences: forward primer (T7prom) SEQ ID No. 8: 5'-TAATACGACTCACTATAGGGAGA-3'; reversed primer (T7ter) SEQ ID No. 9: 5'-CTAGTTATTGCTCAGCGGTG-3'. 1×10$^7$ of lysozyme-processed cells were added into prepared PCR mixture and the mixture was emulsified using modified Williams protocol (Williams et al. 2006). PCR mixture (300 μL) was added to the oil-surfactant mixture (7004 μL) over a period of 2 min and stirring was continued for 5 min. Stirring was carried out at 1,700 rpm on the magnetic stirrer at 4° C.

The lysis of the cells present in an emulsion was conducted using four freeze (10 min at −70° C.)-thaw (10 min at 37° C.) cycles. Emulsion was pipeted into PCR vials as aliquots of 504 μL and PCR was carried out. Additional non-emulsified PCR control was performed. PCR was conducted using the following program: 30 s at 98° C., 35 cycles of −10 s at 98° C., 15 s at 55° C., 45 s at 72° C., and 3 min at 72° C.

After PCR, emulsion was broken using modified Williams method (Williams et al. 2006). Emulsified PCR reactions were pooled into tubes and centrifuged at 16,000 g for 10 min at 37° C. Three extraction steps were performed—two extractions with diethyl ether and one (the middle) extraction with water-saturated ethyl acetate. Residual solvent was vaporized under vacuum.

Nucleic acids were purified using "GeneJET™ PCR Purification Kit" (Thermo Fisher Scientific) using manufacturer's recommended protocol. In order to remove residual plasmid DNA the purified mixture was treated with double-stranded DNA hydrolysing deoxyribonuclease (dsDNase). The mixture was incubated for 5 min at 37° C. Then PCR products were analysed by agarose gel electrophoresis.

The mixture of PCR products was then hydrolysed with appropriate restriction endonucleases and cloned into pre-treated pET28b vector. Ligation mixture was used to transform E. coli DH5α bacteria, single colony plasmid DNA was extracted and selected DNA sequence(s) were identified. Three DNA fragments (EST, D6 it YqfB) were selected.

Then recombinant proteins (EST, D6 and YqfB) having polyhistidine-tag at the N-terminus were purified by affinity chromatography, enzymatic activities of each protein were estimated. It was determined that EST, D6 and YqfB hydrolyse the amide bond of modified dCTP (activity of amidase) as well as behave as esterases.

All three selected proteins are able to hydrolyse the amide bond of N$^4$-modified cytidine nucleotide. The hydrolysis reaction proceeds in various buffer solutions at 37° C. Depending on the concentration of purified protein enzymatic reaction lasts from several minutes to several hours. His tag present in the N-terminus of the protein does not interfere with enzymatic activity. Moreover, these proteins are capable of hydrolysing not only the amide bond of modified dCTP but also the amide bond of modified cytidine.

Conversion of modified cytidine to natural nucleotide is important for several reasons. One of the most promising applications of various modified nucleotides is aptamer technology.

During generation of modified aptamers there is often a need to remove modification group, for example, to amplify aptamer sequences using polymerases which do not interact with modified nucleotides. As a result, aptamers composed of natural nucleotides can be created by using these selective amide bond hydrolysing enzymes (the same approach would be valid for different modification and an appropriate enzyme). Aptamers composed of natural nucleotides can further be easily amplified. This approach eliminates the need to screen or select for mutant polymerase that amplifies modified template.

Detoxification is a very perspective field of medicine that can be closely related to proteins of this invention. For a while, chronic inflammation has been associated with many diseases of aging, but the mechanisms responsible for the production of this inflammation remain unclear. An inflammasome which is an intracellular multiprotein oligomer is responsible for activation of inflammatory processes. The inflammasome triggers the maturation of the inflammatory cytokine interleukin 1β (IL-1β) that in conjunction with other molecules and proteins participates in immune and inflammatory response. It was recently determined that N⁴-acetyl-cytidine which is an intracellular nucleotide-derived metabolite is detectable in the blood of patients that suffer from nucleotide metabolism dysfunction, elevated oxidative stress, high rates of hypertension and arterial stiffness (Furman et al. 2017). It was demonstrated that N⁴-acetyl-cytidine activates the NLRC4 inflammasome, induces the production of IL-1µ, activates platelets and neutrophils and elevates blood pressure in mice. Furthermore, in individuals over 85 years of age, the elevated expression of inflammasome gene modules was associated with all-cause mortality. Thus, targeting inflammasome components and various related signalling molecules may ameliorate chronic inflammation and various other age-associated conditions. The fact that N⁴-acetyl-cytidine is involved in the action of inflammatory response promotes generation of drugs that are based on recombinant proteins capable of converting N⁴-acetyl-cytidine to native cytidine. Therefore, esterases of this invention may be utilized for detoxification of older patients.

Amino acid sequences of enzymes of this invention:

```
EST(SEQ ID No. 1):
MSSLFIGQVFAKTPEVQTSDLTGNTTCSNLVGMVIPADEIGLPTSGAT

ITSATLKIVEDGAIKDAEYCEVLGAIHPVDPTAPDINFQVNLPTNWNK

KFLQFGGGYFNGTVRTGLGNPPAGDRKLGKNTPLAQGYVTFGSDSGNS

TAPLDASFGMNDEALKNFAGDQLKKTKDVALALANVRYNAVPDQVYFA

GGSEGGREGLFIVQNFPDEYDGVISVYPVLNWIPKALKDNRDAQALYK

NDGEGWISPEENDLINETVFKACDSLDGVKDGIISNTSECAEKEDKIL

DTLSESLSEKQIEVIKSFNGPMEFDIQLANDFTTMPGYSQLQGADIGR

LFGTRPIPGVPPVVSESVGHVIDEQDALMGVYSDQVIRYKITRNPDFN

TLTFDPNEYREEILKASNLLDVTDPNISEFRENGGKLILVHGTEDEMV

APQGTSDYYSKLVNEFGQESLDEFAQYYLVPGFSHGGGNFTMSANLLG

ALDAWVVNGDVPSNLVAEDQNSATFGRTRPLCEYPTYPQYNGSGDVNS

AASFTCLKADKDKDISASDIQKLIEKFEVDGEFANHGTARSLQAHLDI

LIKLESQERETVDQIVKHTQKFIKLLDNHKKNGKITDHAYNTLKELAE

SYIKQIK

D6(SEQ ID No. 2):
MEQLKFQKNWNNKCSCDFFTTIRLKGPKYTVGKELEMRIYKGGVFQNH

GMIRVASLRPIQLHQINEWISRLDSGLSPEELRSELFYMYKDKVADVN

KVDFYLILCERVKSKPIQNALFSTESTPAHD

YqfB(SEQ ID No. 3):
MQPNDITFFQRFQDDILAGRKTITIRDESESHFKTGDVLRVGRFEDDG

YFCTIEVTATSTVTLDTLTEKHAEQENMTLTELKKVIADIYPGQTQFY

VIEFKCL
```

Example 8

Primer Extension Reaction using Template-Dependent Polymerase

This example describes a method for the synthesis of nucleic acids containing nucleotide modifications provided in this invention inside the nucleic acid sequence.

Primer extension reactions were carried out using modified nucleoside triphosphates (4a-f) and DNA polymerases: Taq DNA polymerase (Thermo Scientific), Klenow (exo⁻) polymerase (Thermo Scientific), Pfu DNA polymerase (Thermo Scientific), KOD DNA polymerase (Merck Millipore), KOD XL DNA polymerase (Merck Millipore), Bsm DNA polymerase (Thermo Scientific). Four different DNA templates were used that contained four natural nucleotides (A, G, C, T) in a row. Sequences of DNA templates:

```
TempA:
                                      (SEQ ID No. 4)
5'-CCGGAATTAAAAtctccctatagtgagtcgtatta-3'(Metabion)

TempG:
                                      (SEQ ID No. 5)
5'-CCGGAATTGGGGtctccctatagtgagtcgtatta-3'(Metabion)

TempC:
                                      (SEQ ID No. 6)
5'-CCGGAATTCCCCtctccctatagtgagtcgtatta-3'(Metabion)

TempT:
                                      (SEQ ID No. 7)
5'-CCGGAATTTTTTtctccctatagtgagtcgtatta-3'(Metabion)
```

Primer sequence:

```
T7pr:
                                      (SEQ ID No. 8)
5'-taatacgactcactatagggaga-3'(Metabion)
```

The primer was labelled at the 5'-end using ³³P-γATP (TriLink Biotechnologies). 20 pmol of ³³P-γATP was used to label 20 pmol of primer using T4 polynucleotide kinase (Thermo Scientific). Reaction was incubated in a buffer solution containing 50 mM Tris-HCl (pH 7.6 at 25° C.), 10 mM MgCl$_2$, 5 mM DTT and 0.1 mM spermidine for 20 min at 37° C. Reaction was inhibited by adding 1 µL 0.5 M EDTA (pH 8.0) and heating for 10 min at 80° C. For the primer extension assay using various DNA polymerases single-stranded labelled primer was annealed to the single-stranded DNA template. Annealing was performed using equal quantities (5 pmol) of primer and DNA template and heating for 1 min at 95° C. and slowly cooling to room temperature. Desalting of primer and DNA template hybrid was performed using Zeba™ Spin 7K MWCO columns (Thermo Scientific).

The primer extension assay was carried out in 20 mM glutamate (pH 8.2 at 25° C.), 10 mM DTT, 0.5% Triton X-100, 20 mM NaCl, 1 mM MgCl$_2$ buffer solution or other polymerase specific buffer solution using 5 nM of primer and template (TempA, TempT, TempG or TempC) hybrid, 50 nM of DNA polymerase, 0.01 units of inorganic pyrophosphatase (Thermo Scientific) and 10 µM each nucleotide (dATP, dGTP, dCTP, dTTP/dUTP or its modified analogues). Reactions were incubated for 5-60 min at 37° C. using Taq, Klenow (exo⁻), Pfu, KOD, KOD XL polymerases or at 60° C. for Bsm polymerase. Reactions were inhibited by adding double amount (v/v) of STOP solution (95% (v/v) formamide, 0.5 M EDTA, 0.6% (w/v) bromphenol blue and xylene cyanol).

After reactions were completed, samples were incubated for 2-5 min at 95° C. and chilled on ice. Samples were separated on 15% denaturing (8 M urea) polyacrylamide gel in TBE buffer solution (89 mM Tris, 89 mM boric acid, 2 mM EDTA (pH 8.3)). After electrophoresis gel was soaked for 15 min in 10% acetic acid solution and washed for 15 min under running tap water. Gel was placed on a 3 MM CHR Whatman™ chromatographic paper (GE, Healthcare Life Sciences) and dried in vacuum dryer. Finally, the gel was kept on imaging plate for ~16 hours and the results were visualized using Fujifilm FLA-5100 imaging system.

Example 9

Primer Extension Reaction using Template-Independent Polymerase

This example describes a method for the synthesis of nucleic acids containing nucleotide modifications provided in this invention at the 3'-end of nucleic acid sequence.

Primer extension reactions were carried out using modified nucleoside triphosphates (4a-f) and terminal deoxynucleotidyl transferase (TdT) (Thermo Scientific). DNA primer sequence: T7pr: 5'-taatacgactcactataggqaga-3' (SEQ ID No. 8) (Metabion)

The primer was labelled at the 5'-end using $^{33}$P-γATP (TriLink Biotechnologies). 20 pmol of $^{33}$P-γATP was used to label 20 pmol of primer using T4 polynucleotide kinase (Thermo Scientific). Reaction was incubated in buffer solution containing 50 mM Tris-HCl (pH 7.6 at 25° C.), 10 mM MgCl$_2$, 5 mM DTT and 0.1 mM spermidine for 20 min at 37° C. Reaction was inhibited by adding 1 μL 0.5 M EDTA (pH 8.0) and heating for 10 min at 80° C. For the primer extension assay using TdT labelled primer was diluted to the concentration of 100 nM and desalted using Zeba™ Spin 7K MWCO columns (Thermo Scientific).

The primer extension assay using TdT was carried out in 20 mM glutamate (pH 8.2 at 25° C.), 10 mM DTT, 0.5% Triton X-100, 20 mM NaCl, 1 mM MgCl$_2$ buffer solution or commercial TdT buffer solution (200 mM potassium cacodilate (pH 7.2 at 25° C.), 25 mM Tris, 0.01% Triton X-100, 1 mM MgCl$_2$) using 5 nM of primer, 50 nM of TdT and 10 μM of one nucleotide (dATP, dGTP, dCTP, dTTP/dUTP or its modified analogues). Reactions were incubated for 5-15 min at 37° C. Reactions were inhibited by adding double amount (v/v) of STOP solution (95% (v/v) formamide, 0.5 M EDTA, 0.6% (w/v) bromphenol blue and xylene cyanol).

After reactions were completed, samples were incubated for 2-5 min at 95° C. and chilled on ice. Samples were separated on 15% denaturing (8 M urea) polyacrylamide gel (PAGE) in TBE buffer solution (89 mM Tris, 89 mM boric acid, 2 mM EDTA (pH 8.3)). After electrophoresis gel was soaked for 15 min in 10% acetic acid solution and washed for 15 min under running tap water. Gel was placed on a 3 MM CHR Whatman™ chromatographic paper (GE, Healthcare Life Sciences) and dried in a vacuum dryer. Finally, the gel was kept on imaging plate for ~16 hours and the results were visualized using Fujifilm FLA-5100 imaging system.

Example 10

Cross-Linking of Benzophenone Containing Oligonucleotide to Protein

This example demonstrates that benzophenone modification containing oligonucleotides can be covalently cross-linked to a protein that interacts with modified section of an oligonucleotide, and it can be used to study DNA-protein interactions.

First of all, 5'-$^{33}$P-labelled primers are used to synthesize 3'-modified oligonucleotides. N$^4$-benzoyl-3-benzoyl-dCTP (4e) and TdT were used for the synthesis as described in Example 9. Following reaction, TdT was inactivated by heating as recommended by manufacturer. UV cross-linking equipment was assembled with slight modifications as described previously (Sontheimer 1994). It consisted of an ice container, 96-well plate, a sheet of parafilm and a UV light source. A sheet of parafilm was placed over the top of 96-well plate, and taped to the plate on all four sides. Each well was pressed to create a shallow groove. Reaction mixtures were transferred as 10 μL drops to the wells on the parafilm tape. The ice container was placed underneath a 365 nm UV, so that the samples were 1 cm from the surface of the light source. Samples were irradiated at 365 ±5 nm for 5 min.

After irradiation the samples were supplemented with SDS loading dye, heated for 5 min at 95° C., and analysed by electrophoresis on a 14% w/v SDS-PAGE gel. Proteins were stained with Coomasie Briliant Blue staining solution. To examine TdT-oligonucleotide cross-links generated by irradiation, the gel was placed on a 3 MM CHR Whatman™ chromatographic paper (GE, Healthcare Life Sciences) and dried in vacuum dryer. Finally, the gel was kept on imaging plate for ~16 hours and the results were visualized using Fujifilm FLA-5100 imaging system.

PAGE analysis revealed a new band with molecular mass corresponding to the sum of molecular masses of TdT and modified oligonucleotide.

Example 11

Cross-Linking of Benzophenone Containing Oligonucleotide to Polymeric Surfaces

This example shows that N$^4$-benzophenone-modified cytidine containing ON can be covalently cross-linked to a polymeric surface, and it can be used for photoimmobilization of nucleic acids. As used herein, the term "polymeric surface" refers to polystyrene, polypropylene, polylactate, polydimethylsiloxane or polystyrene-, polypropylene-, polylactate-, polydimethylsiloxane-based materials.

Initially, 5'-$^{33}$P-labeled primers are used to synthesize 3'-modified ONs. N$^4$-acetyl-3-benzoyl-dCTP (4b) or N$^4$-benzoyl-3-benzoyl-dCTP (4c) and TdT were used for the synthesis as described in Example 6. Following reaction, TdT was inactivated by heating as recommended by manufacturer.

After TdT inactivation, the reaction mixtures were chilled on ice and transferred as 2 μL drops onto a slide of polymeric solid support. Then the specimens were placed under the UV light source (5 mm away from the surface of the light source) and irradiated for 5 min (365±5 nm). Immediately after irradiation, the specimens were rinsed with 500 μL of wash buffer (50 mM potassium phosphate, 1% Triton X-100 (pH 7.0)) following incubation (1 h at room temperature) in 1.5 mL of wash buffer vigorously shaking. Then the specimens were rinsed with 200 μL of distilled water and air-dried. Photochemical immobilization of modified ONs to polymeric solid supports was then visualized by phosphor imaging.

Example 12

Cross-Linking of Benzophenone Containing Oligonucleotide to Inorganic Surfaces

This example demonstrates that N$^4$-benzophenone-modified cytidine containing ON can be covalently cross-linked to an inorganic surface, and it can be used for photoimmobilization of nucleic acids. As used herein, the term "inorganic surface" refers to silicate glass or other glass-based materials.

Initially, 5'-$^{33}$P-labeled primers are used to synthesize 3'-modified ONs. N$^4$-acetyl-3-benzoyl-dCTP (4b) or N$^4$-benzoyl-3-benzoyl-dCTP (4c) and TdT were used for the synthesis as described in Example 6. Following reaction, TdT was inactivated by heating as recommended by manufacturer.

After TdT inactivation, the reaction mixtures were chilled on ice and transferred as 2 µL drops onto a slide of solid glass support. Then the specimens were placed under the UV light source (5 mm away from the surface of the light source) and irradiated for 5 min (365±5 nm). Immediately after irradiation, the specimens were rinsed with 500 µL of wash buffer (50 mM potassium phosphate, 1% Triton X-100 (pH 7.0)) following incubation (1 h at room temperature) in 1.5 mL of wash buffer vigorously shaking. Then the specimens were rinsed with 200 µL of distilled water and airdried. Photochemical immobilization of modified ONs to polymeric solid supports was then visualized by phosphor imaging.

REFERENCES

1. Alberti, Patrizia, Paola B. Arimondo, Jean-Louis Mergny, Thérèse Garestier, Claude Hélène, ir Jian-Sheng Sun. 2002. "A Directional Nucleation-Zipping Mechanism for Triple Helix Formation". *Nucleic Acids Research* 30 (24): 5407-15.
2. Avino, Anna, Carme Fabrega, Maria Tintore, ir Ramon Eritja. 2012. "Thrombin Binding Aptamer, More than a Simple Aptamer: Chemically Modified Derivatives and Biomedical Applications." *Current Pharmaceutical Design* 18 (14): 2036-47.
3. Balzarini, J., M. Baba, R. Pauwels, P. Herdewijn, S. G. Wood, M. J. Robins, ir E. de Clercq. 1988. "Potent and Selective Activity of 3'-Azido-2,6-Diaminopurine-2',3'-Dideoxyriboside, 3'-Fluoro-2,6-Diaminopurine-2',3'-Dideoxyriboside, and 3'-Fluoro-2',3'-Dideoxyguanosine against Human Immunodeficiency Virus." *Molecular Pharmacology* 33 (3): 243-49.
4. Beigelman, L., J. A. McSwiggen, K. G. Draper, C. Gonzalez, K. Jensen, A. M. Karpeisky, A. S. Modak, J. Matulic-Adamic, A. B. DiRenzo, ir P. Haeberli. 1995. "Chemical Modification of Hammerhead Ribozymes. Catalytic Activity and Nuclease Resistance." *The Journal of Biological Chemistry* 270 (43): 25702-8.
5. Bergen, Konrad, Anna-Lena Steck, Stefan Strutt, Anna Baccaro, Wolfram Welte, Kay Diederichs, ir Andreas Marx. 2012. "Structures of KlenTaq DNA Polymerase Caught While Incorporating C5-Modified Pyrimidine and C7-Modified 7-Deazapurine Nucleoside Triphosphates." *Journal of the American Chemical Society* 134 (29): 11840-43. doi:10.1021/ja3017889.
6. Braasch, D. A., ir D. R. Corey. 2001. "Locked Nucleic Acid (LNA): Fine-Tuning the Recognition of DNA and RNA." *Chemistry & Biology* 8 (1): 1-7.
7. Bryant, M. L., E. G. Bridges, L. Placidi, A. Faraj, A. G. Loi, C. Pierra, D. Dukhan, et al. 2001. "Antiviral L-Nucleosides Specific for Hepatitis B Virus Infection." *Antimicrobial Agents and Chemotherapy* 45 (1): 229-35. doi:10.1128/AAC.45.1.229-235.2001.
8. Buhr, C. A., R. W. Wagner, D. Grant, ir B. C. Froehler. 1996. "Oligodeoxynucleotides Containing C-7 Propyne Analogs of 7-Deaza-2'-Deoxyguanosine and 7-Deaza-2'-Deoxyadenosine." *Nucleic Acids Research* 24 (15): 2974-80.
9. Bumcrot, David, Muthiah Manoharan, Victor Koteliansky, ir Dinah W. Y. Sah. 2006. "RNAi Therapeutics: A Potential New Class of Pharmaceutical Drugs." *Nature Chemical Biology* 2 (12): 711-19. doi:10.1038/nchembio839.
10. Chang, Yun Min, Michael J. Donovan, ir Weihong Tan. 2013. "Using Aptamers for Cancer Biomarker Discovery." *Journal of Nucleic Acids* 2013: 817350. doi: 10.1155/2013/817350.
11. Chelliserrykattil, Jijumon, ir Andrew D. Ellington. 2004. "Evolution of a T7 RNA Polymerase Variant That Transcribes 2'-O-Methyl RNA." *Nature Biotechnology* 22 (9): 1155-60. doi:10.1038/nbt1001.
12. Chen, Hongxia, Yafei Hou, Fangjie Qi, Jiangjiang Zhang, Kwangnak Koh, Zhongming Shen, ir Genxi Li. 2014. "Detection of Vascular Endothelial Growth Factor Based on Rolling Circle Amplification as a Means of Signal Enhancement in Surface Plasmon Resonance." *Biosensors & Bioelectronics* 61 (lapkričio): 83-87. doi: 10.1016/j.bios.2014.05.005.
13. Chen, Tingjian, ir Floyd E. Romesberg. 2014. "Directed Polymerase Evolution." *FEBS Letters* 588 (2): 219-29. doi:10.1016/j.febslet.2013.10.040.
14. Chery, Jessica. 2016. "RNA Therapeutics: RNAi and Antisense Mechanisms and Clinical Applications." *Post-doc Journal: A Journal of Postdoctoral Research and Postdoctoral Affairs* 4 (7): 35-50.
15. Chin, Jason W., Andrew B. Martin, David S. King, Lei Wang, ir Peter G. Schultz. 2002. "Addition of a Photo-crosslinking Amino Acid to the Genetic Code of *Escherichia coli.*" *Proceedings of the National Academy of Sciences of the United States of America* 99 (17): 11020-24. doi:10.1073/pnas.172226299.
16. Craig, M. E., D. M. Crothers, ir P. Doty. 1971. "Relaxation Kinetics of Dimer Formation by Self Complementary Oligonucleotides." *Journal of Molecular Biology* 62 (2): 383-401.
17. Darmostuk, Mariia, Silvie Rimpelova, Helena Gbelcova, ir Tomas Ruml. 2015. "Current Approaches in SELEX: An Update to Aptamer Selection Technology." *Biotechnology Advances* 33 (6 Pt 2): 1141-61. doi:10.1016/j.biotechadv.2015.02.008.
18. De Clercq, E., E. Eckstein, ir T. C. Merigan. 1969. "[Interferon Induction Increased through Chemical Modification of a Synthetic Polyribonucleotide]." *Science (New York, N.Y.)* 165 (3898): 1137-39.
19. De Clercq, Erik, ir Hugh J. Field. 2006. "Antiviral Prodrugs—the Development of Successful Prodrug Strategies for Antiviral Chemotherapy." *British Journal of Pharmacology* 147 (1): 1-11. doi:10.1038/sj.bjp.0706446.
20. Dhende, Vikram P., Satyabrata Samanta, David M. Jones, Ian R. Hardin, ir Jason Locklin. 2011. "One-Step Photochemical Synthesis of Permanent, Nonleaching, Ultrathin Antimicrobial Coatings for Textiles and Plastics." *ACS Applied Materials & Interfaces* 3 (8): 2830-37. doi:10.102/am200324f.
21. Dorman, Gyorgy, Hiroyuki Nakamura, Abigail Pulsipher, ir Glenn D. Prestwich. 2016. "The Life of Pi Star: Exploring the Exciting and Forbidden Worlds of the Benzophenone Photophore." *Chemical Reviews* 116 (24): 15284-398. doi:10.102/acs.chemrev.6b00342.
22. Dorman, G., ir G. D. Prestwich. 2000. "Using Photolabile Ligands in Drug Discovery and Development." *Trends in Biotechnology* 18 (2): 64-77.
23. Elion, G. B., P. A. Furman, J. A. Fyfe, P. de Miranda, L. Beauchamp, ir H. J. Schaeffer. 1977. "Selectivity of Action of an Antiherpetic Agent, 9-(2-Hydroxyethoxymethyl) Guanine." *Proceedings of the National Academy of Sciences of the United States of America* 74 (12): 5716-20.
24. Ellefson, Jared W., Adam J. Meyer, Randall A. Hughes, Joe R. Cannon, Jennifer S. Brodbelt, ir Andrew D. Ellington. 2014. "Directed Evolution of Genetic Parts and Circuits by Compartmentalized Partnered Replication." *Nature Biotechnology* 32 (1): 97-101. doi:10.1038/nbt.2714.
25. Ellington, A. D., ir J. W. Szostak. 1990. "In Vitro Selection of RNA Molecules That Bind Specific Ligands." *Nature* 346 (6287): 818-22. doi:10.1038/346818a0.
26. Flanagan, W. M., A. Kothavale, ir R. W. Wagner. 1996. "Effects of Oligonucleotide Length, Mismatches and mRNA Levels on C-5 Propyne-Modified Antisense Potency." *Nucleic Acids Research* 24 (15): 2936-41.
27. Frank Bennett, C. 2007. "Pharmacological Properties of 2'-O-Methoxyethyl-Modified Oligonucleotides". *Antisense Drug Technology*, 273-303. CRC Press. https://doi.org/10.1201/9780849387951.pta.
28. Furman, David, Junlei Chang, Lydia Lartigue, Christopher R. Bolen, Francois Haddad, Brice Gaudilliere, Edward A. Ganio, et al. 2017. "Expression of Specific Inflammasome Gene Modules Stratifies Older Individuals into Two Extreme Clinical and Immunological States." *Nature Medicine* 23 (2): 174-84. doi:10.1038/nm.4267.
29. Gao, Shunxiang, Xin Zheng, Binghua Jiao, ir Lianghua Wang. 2016. "Post-SELEX Optimization of Aptamers." *Analytical and Bioanalytical Chemistry* 408 (17): 4567-73. doi:10.100⁷/s00216-016-9556-2.
30. Georgiadis, Millie M., Isha Singh, Whitney F. Kellett, Shuichi Hoshika, Steven A. Benner, ir Nigel G. J. Richards. 2015. "Structural Basis for a Six Nucleotide Genetic Alphabet." *Journal of the American Chemical Society* 137 (21): 6947-55. doi:10.1021/jacs.5b03482.
31. Ghadessy, F. J., J. L. Ong, ir P. Holliger. 2001. "Directed Evolution of Polymerase Function by Compartmentalized Self-Replication." *Proceedings of the National Academy of Sciences of the United States of America* 98 (8): 4552-57. doi:10.1073/pnas.071052198.
32. Herdewijn, P., J. Balzarini, E. De Clercq, R. Pauwels, M. Baba, S. Broder, ir H. Vanderhaeghe. 1987. "3'-Substituted 2',3'-Dideoxynucleoside Analogues as Potential Anti-HIV (HTLV-III/LAV) Agents." *Journal of Medicinal Chemistry* 30 (8): 1270-78.
33. Herman, Christine T., Gregory K. Potts, Madeline C. Michael, Nicole V. Tolan, ir Ryan C. Bailey. 2011. "Probing Dynamic Cell-Substrate Interactions Using Photochemically Generated Surface-Immobilized Gradients: Application to Selectin-Mediated Leukocyte Rolling." *Integrative Biology: Quantitative Biosciences from Nano to Macro* 3 (7): 779-91. doi:10.1039/c0ib00151a.
34. Hippel, P. H. von, ir O. G. Berg. 1986. "On the Specificity of DNA-Protein Interactions." *Proceedings of the National Academy of Sciences of the United States of America* 83 (6): 1608-12.
35. Hong, H., S. Goel, Y. Zhang, ir W. Cai. 2011. "Molecular Imaging with Nucleic Acid Aptamers." *Current Medicinal Chemistry* 18 (27): 4195-4205.
36. Hurwitz, Selwyn J., ir Raymond F. Schinazi. 2013. "Prodrug Strategies for Improved Efficacy of Nucleoside Antiviral Inhibitors." *Current Opinion in HIV and AIDS* 8 (6): 556-64. doi:10.1097/COH.0000000000000007.
37. Yamashige, Rie, Michiko Kimoto, Yusuke Takezawa, Akira Sato, Tsuneo Mitsui, Shigeyuki Yokoyama, ir Ichiro Hirao. 2012. "Highly Specific Unnatural Base Pair Systems as a Third Base Pair for PCR Amplification." *Nucleic Acids Research* 40 (6): 2793-2806. doi:10.1093/nar/gkr1068.
38. Yu, Rosie Z, Richard S Geary, Andrew Siwkowski, ir Arthur A Levin. 2007. "Pharmacokinetic/Pharmacodynamic Properties of Phosphorothioate 2'-O-(2-Methoxyethyl)-Modified Antisense Oligonucleotides in Animals and Man". *Antisense Drug Technology*, 305-26. CRC Press. https://doi.org/10.1201/9780849387951.ch11.
39. Jackel, Christian, Peter Kast, ir Donald Hilvert. 2008. "Protein Design by Directed Evolution." *Annual Review of Biophysics* 37: 153-73. doi:10.1146/annurev.biophys.37.032807.125832.
40. Jung, Yun Kyung, Taemin Lee, Eeseul Shin, ir Byeong-Su Kim. 2013. "Highly Tunable Aptasensing Microarrays with Graphene Oxide Multilayers." *Scientific Reports* 3 (lapkričio): 3367. doi:10.1038/srep03367.
41. Keefe, Anthony D., ir Sharon T. Cload. 2008. "SELEX with Modified Nucleotides." *Current Opinion in Chemical Biology* 12 (4): 448-56. doi:10.1016/j.cbpa.2008.06.028.
42. Khanum, Shaukath A., Sheena Shashikanth, ir A. V. Deepak. 2004. "Synthesis and Anti-Inflammatory Activity of Benzophenone Analogues." *Bioorganic Chemistry* 32 (4): 211-22. doi:10.1016/j.bioorg.2004.04.003.
43. Khoury, George A., James Smadbeck, Chris A. Kieslich, ir Christodoulos A. Floudas. 2014. "Protein Folding and de Novo Protein Design for Biotechnological Applications." *Trends in Biotechnology* 32 (2): 99-109. doi: 10.1016/j.tibtech.2013.10.008.
44. Kiilerich-Pedersen, Katrine, Johannes Dapra, Solene Cherre, ir Noemi Rozlosnik. 2013. "High Sensitivity Point-of-Care Device for Direct Virus Diagnostics." *Biosensors & Bioelectronics* 49 (lapkričio): 374-79. doi: 10.1016/j.bios.2013.05.046.
45. Kimoto, Michiko, Rie Yamashige, Ken-ichiro Matsunaga, Shigeyuki Yokoyama, ir Ichiro Hirao. 2013. "Generation of High-Affinity DNA Aptamers Using an Expanded Genetic Alphabet." *Nature Biotechnology* 31 (5): 453-57. doi:10.1038/nbt.2556.
46. Konry, T., A. Novoa, Y. Shemer-Avni, N. Hanuka, S. Cosnier, Arielle Lepellec, ir R. S. Marks. 2005. "Optical Fiber Immunosensor Based on a Poly(pyrrole-Benzophenone) Film for the Detection of Antibodies to Viral Antigen." *Analytical Chemistry* 77 (6): 1771-79. doi: 10.1021/ac048569w.
47. Koshland, Daniel E. 1995. "The Key-Lock Theory and the Induced Fit Theory". *Angewandte Chemie International Edition in English* 33 (23-24): 2375-78. doi: 10.1002/anie.199423751.
48. Kries, Hajo, Rebecca Blomberg, ir Donald Hilvert. 2013. "De Novo Enzymes by Computational Design." *Current Opinion in Chemical Biology* 17 (2): 221-28. doi: 10.1016/j.cbpa.2013.02.012.
49. Kröger, K., A. Jung, S. Reder, ir G. Gauglitz. 2002. "Versatile biosensor surface based on peptide nucleic acid with label free and total internal reflection fluorescence detection for quantification of endocrine disruptors". *Analytica Chimica Acta* 469 (1): 37-48. doi:http://dx.doi.org/10.1016/S0003-2670(02)00470-1.
50. Kusser, W. 2000. "Chemically Modified Nucleic Acid Aptamers for in Vitro Selections: Evolving Evolution." *Journal of Biotechnology* 74 (1): 27-38.
51. Kuwahara, Masayasu, Jun-ichi Nagashima, Masatoshi Hasegawa, Takehiro Tamura, Rina Kitagata, Kazuo Hanawa, Shin-ichi Hososhima, Toshiyuki Kasamatsu, Hiroaki Ozaki, ir Hiroaki Sawai. 2006. "Systematic Characterization of 2'-Deoxynucleoside- 5'-Triphosphate Analogs as Substrates for DNA Polymerases by Polymerase Chain Reaction and Kinetic Studies on Enzymatic Production of Modified DNA". *Nucleic Acids Research* 34 (19): 5383-94. doi:10.1093/nar/gkl637.

52. Lam, Curtis, Christopher Hipolito, ir David M. Perrin. 2008. "Synthesis and Enzymatic Incorporation of Modified Deoxyadenosine Triphosphates". *European Journal of Organic Chemistry* 2008 (29): 4915-23. doi:10.1002/ejoc.200800381.
53. Lang, Kathrin, ir Jason W. Chin. 2014. "Cellular Incorporation of Unnatural Amino Acids and Bioorthogonal Labeling of Proteins." *Chemical Reviews* 114 (9): 4764-4806. doi:10.1021/cr400355w.
54. Langkjaer, Niels, Anna Pasternak, ir Jesper Wengel. 2009. "UNA (unlocked Nucleic Acid): A Flexible RNA Mimic That Allows Engineering of Nucleic Acid Duplex Stability." *Bioorganic & Medicinal Chemistry* 17 (15): 5420-25. doi:10.1016/j.bmc.2009.06.045.
55. Laos, Roberto, J. Michael Thomson, ir Steven A. Benner. 2014. "DNA Polymerases Engineered by Directed Evolution to Incorporate Non-Standard Nucleotides." *Frontiers in Microbiology* 5: 565. doi:10.3389/fmicb.2014.00565.
56. Lapa, Sergey A., Alexander V. Chudinov, ir Edward N. Timofeev. 2016. "The Toolbox for Modified Aptamers." *Molecular Biotechnology* 58 (2): 79-92. doi:10.1007/s12033-015-9907-9.
57. Leemhuis, Hans, Ronan M. Kelly, ir Lubbert Dijkhuizen. 2009. "Directed Evolution of Enzymes: Library Screening Strategies." *IUBMB Life* 61 (3): 222-28. doi:10.1002/iub.165.
58. Lescrinier, E., R. Esnouf, J. Schraml, R. Busson, H. Heus, C. Hilbers, ir P. Herdewijn. 2000. "Solution Structure of a HNA-RNA Hybrid." *Chemistry &Biology* 7 (9): 719-31.
59. Lipi, Farhana, Suxiang Chen, Madhuri Chakravarthy, Shilpa Rakesh, ir Rakesh N. Veedu. 2016. "In Vitro Evolution of Chemically-Modified Nucleic Acid Aptamers: Pros and Cons, and Comprehensive Selection Strategies." *RNA Biology* 13 (12): 1232-45. doi:10.1080/15476286.2016.1236173.
60. Lomakin, A., ir M. D. Frank-Kamenetskii. 1998. "A Theoretical Analysis of Specificity of Nucleic Acid Interactions with Oligonucleotides and Peptide Nucleic Acids (PNAs)." *Journal of Molecular Biology* 276 (1): 57-70. doi:10.1006/jmbi.1997.1497.
61. Malyshev, Denis A., Kirandeep Dhami, Henry T. Quach, Thomas Lavergne, Phillip Ordoukhanian, Ali Torkamani, ir Floyd E. Romesberg. 2012. "Efficient and Sequence-Independent Replication of DNA Containing a Third Base Pair Establishes a Functional Six-Letter Genetic Alphabet." *Proceedings of the National Academy of Sciences of the United States of America* 109 (30): 12005-10. doi: 10.1073/pnas.1205176109.
62. Marcon, Lionel, Mei Wang, Yannick Coffinier, Francois Le Normand, Oleg Melnyk, Rabah Boukherroub, ir Sabine Szunerits. 2010. "Photochemical Immobilization of Proteins and Peptides on Benzophenone-Terminated Boron-Doped Diamond Surfaces." *Langmuir: The ACS Journal of Surfaces and Colloids* 26 (2): 1075-80. doi:10.1021/la903012v.
63. Marwick, C. 1998. "First 'Antisense' Drug Will Treat CMV Retinitis." *JAMA* 280 (10): 871
64. McGowan, Mary P., Jean-Claude Tardif, Richard Ceska, Lesley J. Burgess, Handrean Soran, Ioanna Gouni-Berthold, Gilbert Wagener, ir Scott Chasan-Taber. 2012. "Randomized, Placebo-Controlled Trial of Mipomersen in Patients with Severe Hypercholesterolemia Receiving Maximally Tolerated Lipid-Lowering Therapy." *PloS One* 7 (11): e49006. doi:10.1371/journal.pone.0049006.
65. Meek, Kirsten N., Alexandra E. Rangel, ir Jennifer M. Heemstra. 2016. "Enhancing Aptamer Function and Stability via in Vitro Selection Using Modified Nucleic Acids." *Methods (San Diego, Calif.)* 106 (rugpjūčio): 29-36. doi:10.1016/j.ymeth.2016.03.008.
66. Meisenheimer, K. M., ir T. H. Koch. 1997. "Photocross-Linking of Nucleic Acids to Associated Proteins." *Critical Reviews in Biochemistry and Molecular Biology* 32 (2): 101-40. doi:10.3109/10409239709108550.
67. Monn, Selina T. M., ir Stefan Schurch. 2007. "New Aspects of the Fragmentation Mechanisms of Unmodified and Methylphosphonate-Modified Oligonucleotides." *Journal of the American Society for Mass Spectrometry* 18 (6): 984-90. doi:10.1016/j.jasms.2007.02.006.
68. Moulds, C., J. G. Lewis, B. C. Froehler, D. Grant, T. Huang, J. F. Milligan, M. D. Matteucci, ir R. W. Wagner. 1995. "Site and Mechanism of Antisense Inhibition by C-5 Propyne Oligonucleotides." *Biochemistry* 34 (15): 5044-53.
69. Nakatani, Kazuhiko, Chikara Dohno, ir Isao Saito. 1999. "Synthesis of DNA Oligomers Containing Modified Uracil Possessing Electron-Accepting Benzophenone Chromophore." *The Journal of Organic Chemistry* 64 (18): 6901-4.
70. Nakatani, Kazuhiko, Takashi Yoshida, ir Isao Saito. 2002. "Photochemistry of Benzophenone Immobilized in a Major Groove of DNA: Formation of Thermally Reversible Interstrand Cross-Link." *Journal of the American Chemical Society* 124 (10): 2118-19.
71. Obeid, Samra, Anna Baccaro, Wolfram Welte, Kay Diederichs, ir Andreas Marx. 2010. "Structural Basis for the Synthesis of Nucleobase Modified DNA by Thermus Aquaticus DNA Polymerase." *Proceedings of the National Academy of Sciences of the United States of America* 107 (50): 21327-31. doi:10.1073/pnas.1013804107.
72. Ong, Jennifer L., David Loakes, Szymon Jaroslawski, Kathleen Too, ir Philipp Holliger. 2006. "Directed Evolution of DNA Polymerase, RNA Polymerase and Reverse Transcriptase Activity in a Single Polypeptide." *Journal of Molecular Biology* 361 (3): 537-50. doi:10.1016/j.jmb.2006.06.050.
73. Patel, D. J., ir A. K. Suri. 2000. "Structure, Recognition and Discrimination in RNA Aptamer Complexes with Cofactors, Amino Acids, Drugs and Aminoglycoside Antibiotics." *Journal of Biotechnology* 74 (1): 39-60.
74. Petersen, Michael, ir Jesper Wengel. 2003. "LNA: A Versatile Tool for Therapeutics and Genomics." *Trends in Biotechnology* 21 (2): 74-81. doi:10.1016/S0167-7799 (02)00038-0.
75. Pokorski, Jonathan K., Mark A. Witschi, Bethany L. Purnell, ir Daniel H. Appella. 2004. "(S,S)-trans-Cyclopentane-Constrained Peptide Nucleic Acids. A General Backbone Modification that Improves Binding Affinity and Sequence Specificity". *Journal of the American Chemical Society* 126 (46): 15067-73. doi:10.1021/ja046280q.
76. Rahman, S. M. Abdur, Takeshi Baba, Tetsuya Kodama, Md Ariful Islam, ir Satoshi Obika. 2012. "Hybridizing Ability and Nuclease Resistance Profile of Backbone Modified Cationic Phosphorothioate Oligonucleotides." *Bioorganic & Medicinal Chemistry* 20 (13): 4098-4102. doi:10.1016/j.bmc.2012.05.009.
77. Rayburn, Elizabeth R., ir Ruiwen Zhang. 2008. "Antisense, RNAi, and Gene Silencing Strategies for Therapy: Mission Possible or Impossible?" *Drug Discovery Today* 13 (11-12): 513-21. doi:10.1016/j.drudis.2008.03.014.

78. Rakesh N. Veedu, ir Jesper Wengel. 2010. "Locked Nucleic Acids: Promising Nucleic Acid Analogs for Therapeutic Applications." *Chemistry & Biodiversity* 7 (3): 536-42. doi:10.1002/cbdv.200900343.
79. Ranganatha, V Lakshmi, B R Vijay Avin, Prabhu Thirusangu, T Prashanth, B T Prabhakar, ir Shaukath Ara Khanum. 2013. "Synthesis, angiopreventive activity, and in vivo tumor inhibition of novel benzophenone-benzimidazole analogs". *Life sciences* 93 (23): 904-911. doi:10.1016/j.lfs.2013.10.001.
80. Ratilainen, T., A. Holmen, E. Tuite, P. E. Nielsen, ir B. Norden. 2000. "Thermodynamics of Sequence-Specific Binding of PNA to DNA." *Biochemistry* 39 (26): 7781-91.
81. Renberg, Bjorn, Kae Sato, Kazuma Mawatari, Naokazu Idota, Takehiko Tsukahara, ir Takehiko Kitamori. 2009. "Serial DNA Immobilization in Micro- and Extended Nanospace Channels." *Lab on a chip* 9 (11): 1517-23. doi:10.1039/b823436a.
82. Renneberg, Dorte, ir Christian J. Leumann. 2002. "Watson-Crick Base-Pairing Properties of Tricyclo-DNA." *Journal of the American Chemical Society* 124 (21): 5993-6002.
83. Rohloff, John C., Amy D. Gelinas, Thale C. Jarvis, Urs A. Ochsner, Daniel J. Schneider, Larry Gold, ir Nebojsa Janjic. 2014. "Nucleic Acid Ligands With Protein-like Side Chains: Modified Aptamers and Their Use as Diagnostic and Therapeutic Agents." *Molecular Therapy. Nucleic Acids* 3 (spalio): e201. doi:10.1038/mtna.2014.49.
84. Rotherham, Lia S., Charlotte Maserumule, Keertan Dheda, Jacques Theron, ir Makobetsa Khati. 2012. "Selection and Application of ssDNA Aptamers to Detect Active TB from Sputum Samples." *PloS One* 7 (10): e46862. doi:10.1371/journal.pone.0046862.
85. Rougee, M., B. Faucon, J. L. Mergny, F. Barcelo, C. Giovannangeli, T. Garestier, ir C. Helene. 1992. "Kinetics and thermodynamics of triple-helix formation: effects of ionic strength and mismatched". *Biochemistry* 31 (38): 9269-78. doi:10.1021/bi00153a021.
86. Samish, Ilan, Christopher M. MacDermaid, Jose Manuel Perez-Aguilar, ir Jeffery G. Saven. 2011. "Theoretical and Computational Protein Design." *Annual Review of Physical Chemistry* 62: 129-49. doi:10.1146/annurev-physchem-032210-103509.
87. Sastry, S., ir B. M. Ross. 1998. "RNA-Binding Site in T7 RNA Polymerase." *Proceedings of the National Academy of Sciences of the United States of America* 95 (16): 9111-16.
88. Sastry, S. S., H. P. Spielmann, Q. S. Hoang, A. M. Phillips, A. Sancar, ir J. E. Hearst. 1993. "Laser-Induced Protein-DNA Cross-Links via Psoralen Furanside Monoadducts." *Biochemistry* 32 (21): 5526-38.
89. Schaeffer, H. J., L. Beauchamp, P. de Miranda, G. B. Elion, D. J. Bauer, ir P. Collins. 1978."9-(2-Hydroxyethoxymethyl) Guanine Activity against Viruses of the Herpes Group." *Nature* 272 (5654): 583-85.
90. Seo, Young Jun, Denis A. Malyshev, Thomas Lavergne, Phillip Ordoukhanian, ir Floyd E. Romesberg. 2011. "Site-Specific Labeling of DNA and RNA Using an Efficiently Replicated and Transcribed Class of Unnatural Base Pairs." *Journal of the American Chemical Society* 133 (49): 19878-88. doi:10.1021/ja207907d.
91. Sergentu, Dumitru-Claudiu, Remi Maurice, Remco W. A. Havenith, Ria Broer, ir Daniel Roca-Sanjuan. 2014. "Computational Determination of the Dominant Triplet Population Mechanism in Photoexcited Benzophenone." *Physical Chemistry Chemical Physics: PCCP* 16 (46): 25393-403. doi:10.1039/c4cp03277b.
92. Sharma, Vivek K., Pallavi Rungta, ir Ashok K. Prasad. 2014. "Nucleic acid therapeutics: basic concepts and recent developments". *RSC Adv.* 4 (32): 16618-31. doi:10.1039/C3RA47841 F.
93. Sharma, Vivek K., Raman K. Sharma, ir Sunil K. Singh. 2014. "Antisense oligonucleotides: modifications and clinical trials". *Med. Chem. Commun.* 5 (10): 1454-71. doi:10.1039/C4MD00184B.
94. Shigdel, Uddhav Kumar, Junliang Zhang, ir Chuan He. 2008. "Diazirine-Based DNA Photo-Cross-Linking Probes for the Study of Protein-DNA Interactions." *Angewandte Chemie (International Ed. in English)* 47 (1): 90-93. doi:10.1002/anie.200703625.
95. Shin, Seonmi, Il-Hyun Kim, Wonchull Kang, Jin Kuk Yang, ir Sang Soo Hah. 2010. "An Alternative to Western Blot Analysis Using RNA Aptamer-Functionalized Quantum Dots." *Bioorganic & Medicinal Chemistry Letters* 20 (11): 3322-25. doi:10.1016/j.bmcl.2010.04.040.
96. Shoji, Y., S. Akhtar, A. Periasamy, B. Herman, ir R. L. Juliano. 1991. "Mechanism of Cellular Uptake of Modified Oligodeoxynucleotides Containing Methylphosphonate Linkages." *Nucleic Acids Research* 19 (20): 5543-50.
97. Sontheimer, E. J. 1994. "Site-Specific RNA Crosslinking with 4-Thiouridine." *Molecular Biology Reports* 20 (1): 35-44.
98. Sosic, Alice, Anna Meneghello, Agnese Antognoli, Erica Cretaio, ir Barbara Gatto. 2013. "Development of a Multiplex Sandwich Aptamer Microarray for the Detection of VEGF165 and Thrombin." *Sensors (Basel, Switzerland)* 13 (10): 13425-38. doi:10.3390/s131013425.
99. Steen, Hanno, ir Ole Norregaard Jensen. 2002. "Analysis of Protein-Nucleic Acid Interactions by Photochemical Cross-Linking and Mass Spectrometry." *Mass Spectrometry Reviews* 21 (3): 163-82. doi:10.1002/mas.10024.
100. Summerton, James. 1989. "Uncharged nucleic acid analogs for therapeutic and diagnostic applications: Oligomers assembled from ribosederived subunits". *Discoveries in Antisense Nucleic Acids,* 71-80.
101. Sun, Hongguang, ir Youli Zu. 2015. "A Highlight of Recent Advances in Aptamer Technology and Its Application." *Molecules (Basel, Switzerland)* 20 (7): 11959-80. doi:10.3390/molecules200711959.
102. Tolle, Fabian, Gerhard M. Brandle, Daniel Matzner, ir Gunter Mayer. 2015. "A Versatile Approach Towards Nucleobase-Modified Aptamers." *Angewandte Chemie (International Ed. in English)* 54 (37): 10971-74. doi:10.1002/anie.201503652.
103. Tombelli, S., M. Minunni, ir M. Mascini. 2005. "Analytical Applications of Aptamers." *Biosensors & Bioelectronics* 20 (12): 2424-34. doi:10.1016/j.bios.2004.11.006.
104. Traut, R. R., A. Bollen, T. T. Sun, J. W. Hershey, J. Sundberg, ir L. R. Pierce. 1973. "Methyl 4-Mercaptobutyrimidate as a Cleavable Cross-Linking Reagent and Its Application to the *Escherichia coli* 30S Ribosome." *Biochemistry* 12 (17): 3266-73.
105. Tucker, C. E., L. S. Chen, M. B. Judkins, J. A. Farmer, S. C. Gill, ir D. W. Drolet. 1999. "Detection and Plasma Pharmacokinetics of an Anti-Vascular Endothelial Growth Factor Oligonucleotide-Aptamer (NX1838) in Rhesus Monkeys." *Journal of Chromatography. B, Biomedical Sciences and Applications* 732 (1): 203-12.
106. Tuerk, C., ir L. Gold. 1990. "Systematic Evolution of Ligands by Exponential Enrichment: RNA Ligands to Bacteriophage T4 DNA Polymerase." *Science (New York, N.Y.)* 249 (4968): 505-10.

107. Turgeon, Aurora J., Brendan A. Harley, ir Ryan C. Bailey. 2014. "Benzophenone-Based Photochemical Micropatterning of Biomolecules to Create Model Substrates and Instructive Biomaterials." *Methods in Cell Biology* 121: 231-42. doi:10.1016/B978-0-12-800281-0.00015-4.
108. Veedu, Rakesh N., ir Jesper Wengel. 2009. "Locked Nucleic Acid as a Novel Class of Therapeutic Agents." *RNA Biology* 6 (3): 321-23.
109. Wang, L., A. Brock, B. Herberich, ir P. G. Schultz. 2001. "Expanding the Genetic Code of *Escherichia coli.*" *Science (New York, N.Y.)* 292 (5516): 498-500. doi:10.1126/science.1060077.
110. Wang, Qing, Wei Liu, Yuqian Xing, Xiaohai Yang, Kemin Wang, Rui Jiang, Pei Wang, ir Qing Zhao. 2014. "Screening of DNA Aptamers against Myoglobin Using a Positive and Negative Selection Units Integrated Microfluidic Chip and Its Biosensing Application." *Analytical Chemistry* 86 (13): 6572-79. doi:10.102/ac501088q.
111. Weiler, J., H. Gausepohl, N. Hauser, O. N. Jensen, ir J. D. Hoheisel. 1997. "Hybridisation Based DNA Screening on Peptide Nucleic Acid (PNA) Oligomer Arrays." *Nucleic Acids Research* 25 (14): 2792-99.
112. Williams, Richard, Sergio G. Peisajovich, Oliver J. Miller, Shlomo Magdassi, Dan S. Tawfik, ir Andrew D. Griffiths. 2006. "Amplification of Complex Gene Libraries by Emulsion PCR." *Nature Methods* 3 (7): 545-50. doi:10.1038/nmeth896.
113. Wilson, Charles, ir Anthony D. Keefe. 2006. "Building Oligonucleotide Therapeutics Using Non-Natural Chemistries." *Current Opinion in Chemical Biology* 10 (6): 607-14. doi:10.1016/j.cbpa.2006.10.001.
114. Wower, I., J. Wower, M. Meinke, ir R. Brimacombe. 1981. "The Use of 2-Iminothiolane as an RNA-Protein Cross-Linking Agent in *Escherichia coli* Ribosomes, and the Localisation on 23S RNA of Sites Cross-Linked to Proteins L4, L6, L21, L23, L27 and L29." *Nucleic Acids Research* 9 (17): 4285-4302.
115. Xia, Gang, Liangjing Chen, Takashi Sera, Ming Fa, Peter G. Schultz, ir Floyd E. Romesberg. 2002. "Directed Evolution of Novel Polymerase Activities: Mutation of a DNA Polymerase into an Efficient RNA Polymerase." *Proceedings of the National Academy of Sciences of the United States of America* 99 (10): 6597-6602. doi:10.1073/pnas.102577799.
116. Xie, Xinqiang, Jingdan Liang, Tianning Pu, Fei Xu, Fen Yao, Yan Yang, Yi-Lei Zhao, et al. 2012. "Phosphorothioate DNA as an Antioxidant in Bacteria." *Nucleic Acids Research* 40 (18): 9115-24. doi:10.1093/nar/gks650.
117. Zhao, Qiang, Xing-Fang Li, Yuanhua Shao, ir X. Chris Le. 2008. "Aptamer-Based Affinity Chromatographic Assays for Thrombin." *Analytical Chemistry* 80 (19): 7586-93. doi:10.1021/ac801206s.
118. Patent US20130142796
119. U.S. Pat. No. 5,595,978
120. Patent US20140243389
121. U.S. Pat. No. 5,270,163
122. Patent US20160215013
123. U.S. Pat. No. 7,514,210

The invention claimed is:

1. A compound of structural Formula I:

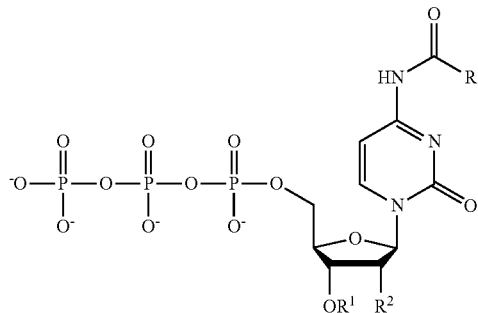

Formula I wherein
R is independently selected from the group consisting of:
—(CH$_2$)$_n$—CH$_3$, wherein n is 4, 5, 6, 7, 8, 9 or 10;

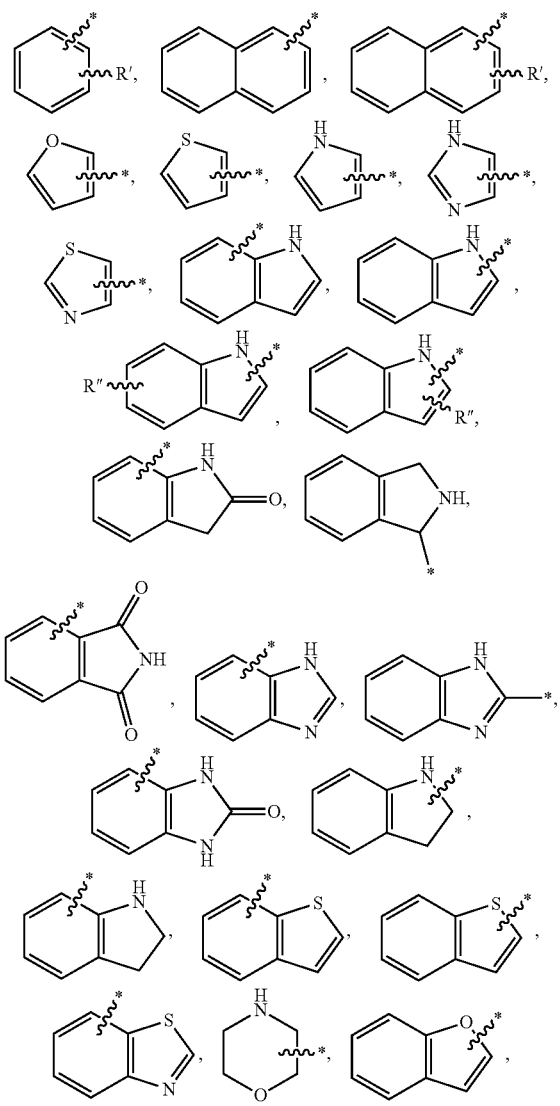

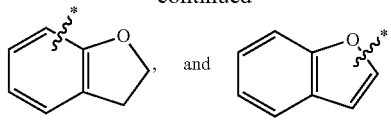

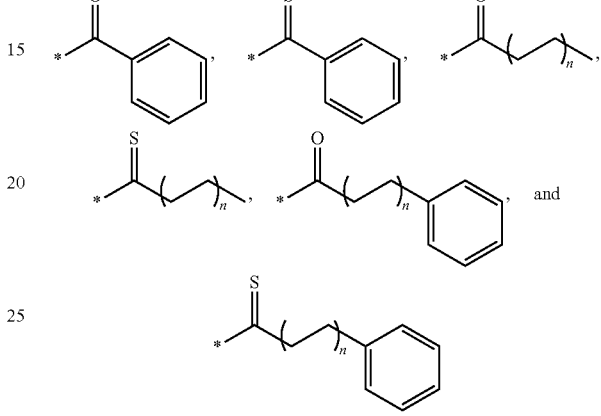

wherein * is the point of attachment of the R group;
wherein R' is independently selected from the group consisting of:

wherein n is 0, 1, 2, 3, 4, 5, 6, 7, 8, 9, or 10; and wherein * is the point of attachment of the R' group to the R group;
R" is independently selected from the group consisting of —H, —CH$_3$, —NH$_2$, —OH, —Cl, and —Br;
R$^1$ is independently selected from the group consisting of —H, —OAc, —OBz, —Me, and —Et;
R$^2$ is independently selected from the group consisting of —H, —OH, —OMe, and —OEt.

2. A method for selection of enzymes using compartmentalized replication comprising:
transforming a collection of cells with a gene library encoding target enzymes and composed of a collection of plasmids each comprising a vector and a gene of interest, wherein the gene library can be a metagenomic library or mutant library;
inducing gene expression of the plasmid-encoded genes;
adding the compound of claim 1 and natural dATP, TTP, and dGTP;
creating an emulsion to compartmentalize individual cells;
lysing the compartmentalized cells;
performing a reaction of conversion of the compound of claim 1;
performing emulsion PCR;
extracting the PCR products; and
sequencing of the PCR products to identify the sequences of the selected enzymes.

3. A nucleic acid comprising a compound according to claim 1.

4. A nucleic acid according to claim 3, wherein the nucleic acid is DNA, RNA or a combination of DNA/RNA.

5. A nucleic acid according to claim 3, wherein the nucleic acid is from 10 to 4000 nucleotides in length.

6. A method for selection of enzymes using compartmentalized replication comprising:

transforming a collection of cells with a gene library encoding target enzymes and composed of a collection of plasmids each comprising a vector and a gene of interest, wherein the gene library can be a metagenomic library or mutant library;

inducing gene expression of the plasmid-encoded genes;

adding the nucleic acid claim 3 and natural dATP, TTP, and dGTP;

creating an emulsion to compartmentalize individual cells;

lysing the compartmentalized cells;

performing a reaction of conversion of the nucleic acid of claim 3;

performing emulsion PCR;

extracting the PCR products; and sequencing of the PCR products to identify the sequences of the selected enzymes.

7. A nucleic acid comprising a compound of structural Formula IA:

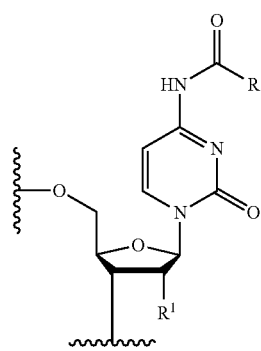

Formula IA wherein

R is independently selected from the group consisting of:
—(CH$_2$)$_n$—CH$_3$, wherein n is 4, 5, 6, 7, 8, 9 or 10;

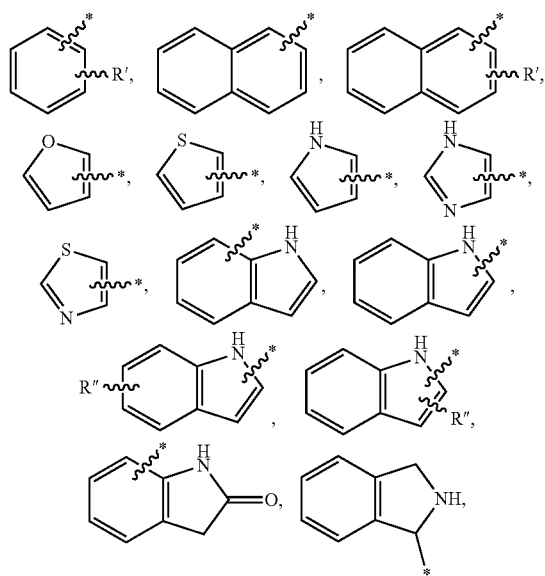

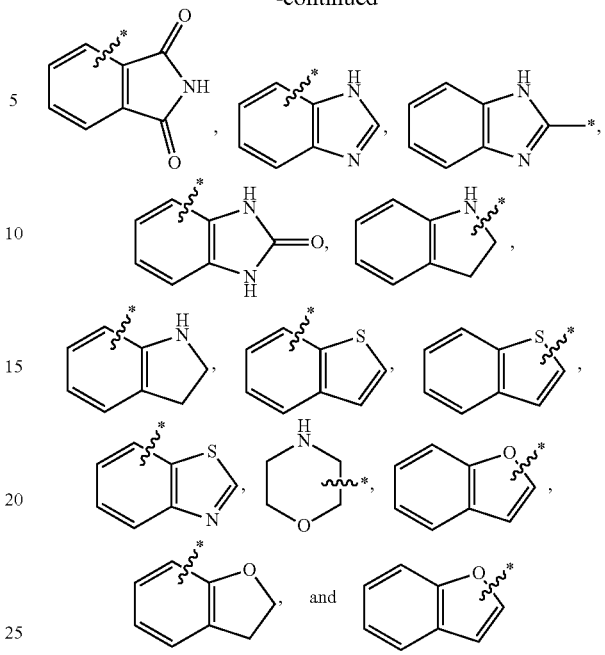

wherein * is the point of attachment of R group;

R' is independently selected from the group consisting of:

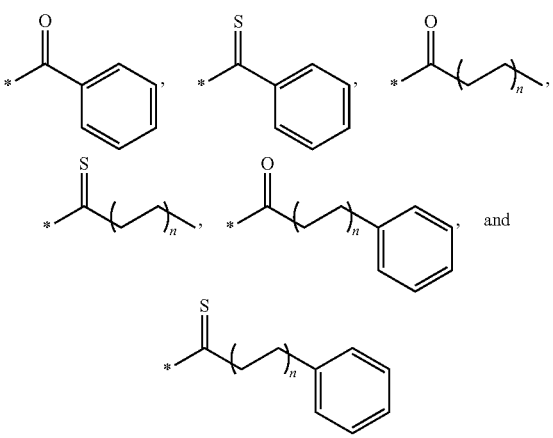

wherein n is 0, 1, 2, 3, 4, 5, 6, 7, 8, 9 or 10; and * is the point of attachment of R' group to the R group;

R" is independently selected from the group consisting of —H, —CH$_3$, —NH$_2$, —OH, —Cl, and —Br;

R$^1$ is independently selected from the group consisting of —H, —OH, —OMe, and —OEt.

8. A method for selection of enzymes using compartmentalized replication comprising:

transforming a collection of cells with a gene library encoding target enzymes and composed of a collection of plasmids each comprising a vector and a gene of interest, wherein the gene library can be a metagenomic library or mutant library;

inducing gene expression of the plasmid-encoded genes;

adding the compound of claim 7 and natural dATP, TTP, and dGTP;

creating an emulsion to compartmentalize individual cells;

lysing the compartmentalized cells;
performing a reaction of conversion of the compound of claim 7;
performing emulsion PCR;
extracting the PCR products; and
sequencing of the PCR products to identify the sequences of the selected enzymes.

9. A nucleic acid comprising a compound according to claim 7.

10. A nucleic acid according to claim 9, wherein the nucleic acid is DNA, RNA or a combination of DNA/RNA.

11. A nucleic acid according to claim 9, wherein the nucleic acid is from 10 to 4000 nucleotides in length.

12. A method for selection of enzymes using compartmentalized replication comprising:
    transforming a collection of cells with a gene library encoding target enzymes and composed of a collection of plasmids each comprising a vector and a gene of interest, wherein the gene library can be a metagenomic library or mutant library;
    inducing gene expression of the plasmid-encoded genes;
    adding the nucleic acid of claim 9 and natural dATP, TTP, and dGTP;
    creating an emulsion to compartmentalize individual cells;
    lysing the compartmentalized cells;
    performing a reaction of conversion of the nucleic acid of claim 9;
    performing emulsion PCR;
    extracting the PCR products; and
    sequencing of the PCR products to identify the sequences of the selected enzymes.

13. A method for cross-linking with macromolecules, organic and inorganic surfaces comprising providing and applying an effective amount of the nucleic acid of claim 9.

14. A method for selection of enzymes using compartmentalized replication comprising:
    transforming a collection of cells with a gene library encoding target enzymes and composed of a collection of plasmids each comprising a vector and a gene of interest, wherein the gene library can be a metagenomic library or mutant library;
    inducing gene expression of the plasmid-encoded genes;
    adding the nucleic acid of claim 4 and natural dATP, TTP, and dGTP;
    creating an emulsion to compartmentalize individual cells;
    lysing the compartmentalized cells;
    performing a reaction of conversion of the nucleic acid of claim 4;
    performing emulsion PCR;
    extracting the PCR products; and
    sequencing of the PCR products to identify the sequences of the selected enzymes.

15. A method for selection of enzymes using compartmentalized replication comprising:
    transforming a collection of cells with a gene library encoding target enzymes and composed of a collection of plasmids each comprising a vector and a gene of interest, wherein the gene library can be a metagenomic library or mutant library;
    inducing gene expression of the plasmid-encoded genes;
    adding the nucleic acid of claim 5 and natural dATP, TTP, and dGTP;
    creating an emulsion to compartmentalize individual cells;
    lysing the compartmentalized cells;
    performing a reaction of conversion of the nucleic of claim 5;
    performing emulsion PCR;
    extracting the PCR products; and
    sequencing of the PCR products to identify the sequences of the selected enzymes.

16. A method for selection of enzymes using compartmentalized replication comprising:
    transforming a collection of cells with a gene library encoding target enzymes and composed of a collection of plasmids each comprising a vector and a gene of interest, wherein the gene library can be a metagenomic library or mutant library;
    inducing gene expression of the plasmid-encoded genes;
    adding the nucleic acid of claim 10 and natural dATP, TTP, and dGTP;
    creating an emulsion to compartmentalize individual cells;
    lysing the compartmentalized cells;
    performing a reaction of conversion of the nucleic of claim 10;
    performing emulsion PCR;
    extracting the PCR products; and
    sequencing of the PCR products to identify the sequences of the selected.

17. A method for selection of enzymes using compartmentalized replication comprising:
    transforming a collection of cells with a gene library encoding target enzymes and composed of a collection of plasmids each comprising a vector and a gene of interest, wherein the gene library can be a metagenomic library or mutant library;
    inducing gene expression of the plasmid-encoded genes;
    adding the nucleic acid of claim 11 and natural dATP, TTP, and dGTP;
    creating an emulsion to compartmentalize individual cells;
    lysing the compartmentalized cells;
    performing a reaction of conversion of the nucleic of claim 11;
    performing emulsion PCR;
    extracting the PCR products; and
    sequencing of the PCR products to identify the sequences of the selected providing and applying an effective amount of the nucleic acid of claim 11.

18. A method for cross-linking with macromolecules, organic and inorganic surfaces comprising providing and applying an effective amount of the nucleic acid of claim 10.

19. A method for cross-linking with macromolecules, organic and inorganic surfaces comprising providing and applying an effective amount of the nucleic acid of claim 11.

* * * * *